(12) United States Patent
DeSilets et al.

(10) Patent No.: US 11,717,460 B2
(45) Date of Patent: *Aug. 8, 2023

(54) SYSTEM, APPARATUS AND METHOD FOR PATIENT POSITIONING PRIOR TO, DURING AND/OR AFTER MEDICAL PROCEDURES

(71) Applicant: Mizuho OSI, Union City, CA (US)

(72) Inventors: Mark Edward DeSilets, San Jose, CA (US); Stephan John Schmid, San Francisco, CA (US); Vincent Hodges, San Jose, CA (US); Peter Thien Van Le, San Jose, CA (US)

(73) Assignee: Mizuho OSI, Union City, CA (US)

( * ) Notice: Subject to any disclaimer, the term of this patent is extended or adjusted under 35 U.S.C. 154(b) by 134 days.

This patent is subject to a terminal disclaimer.

(21) Appl. No.: 17/469,077

(22) Filed: Sep. 8, 2021

(65) Prior Publication Data

US 2021/0401655 A1    Dec. 30, 2021

Related U.S. Application Data

(63) Continuation of application No. 15/912,530, filed on Mar. 5, 2018, now Pat. No. 11,129,765, which is a
(Continued)

(51) Int. Cl.
*A61G 13/12* (2006.01)
*A61B 46/20* (2016.01)
(Continued)

(52) U.S. Cl.
CPC ............ *A61G 13/121* (2013.01); *A61B 46/10* (2016.02); *A61B 46/20* (2016.02); *A61B 46/40* (2016.02);
(Continued)

(58) Field of Classification Search
CPC .... A61G 13/121; A61G 13/101; A61G 13/02; A61B 46/10; A61B 46/40; A61B 46/20;
(Continued)

(56) References Cited

U.S. PATENT DOCUMENTS 3,030,957 A    4/1962 Melges
3,188,079 A    6/1965 Boetcker et al.
(Continued)

FOREIGN PATENT DOCUMENTS

DE    102007035922 A1    5/2009
DE    102010006575 A1    8/2011
(Continued)

OTHER PUBLICATIONS

International Search Report for PCT/US2018/028480, dated Oct. 15, 2018.
(Continued)

*Primary Examiner* — Tarla R Patel
(74) *Attorney, Agent, or Firm* — Reed Smith LLP; Matthew P. Frederick; Anupma Sahay

(57) ABSTRACT

A system for positioning a patient before, during or after a medical procedure can include an arm assembly and a surgical drape for use with the arm assembly. The surgical drape can be configured to be placed around a surgical site where an operative procedure is to be conducted. The surgical drape includes a transparent viewing window, multiple handle covers, and an expandable opening on the top side of the surgical drape. Additionally, the surgical drape may also include adhesive components on the bottom side of the drape that may be independently removed in order to affix the drape around a surgical site.

21 Claims, 31 Drawing Sheets

Related U.S. Application Data continuation-in-part of application No. 15/493,700, filed on Apr. 21, 2017, now Pat. No. 10,905,614.

(51) Int. Cl.

| | |
|---|---|
| *B25J 19/00* | (2006.01) |
| *A61B 46/10* | (2016.01) |
| *A61G 13/10* | (2006.01) |
| *A61G 13/02* | (2006.01) |
| *A61B 46/00* | (2016.01) |
| *B25J 13/02* | (2006.01) |
| *B25J 9/12* | (2006.01) |

(52) U.S. Cl.
CPC ............ *A61G 13/02* (2013.01); *A61G 13/101* (2013.01); *B25J 19/0075* (2013.01); *A61B 2046/205* (2016.02); *B25J 9/126* (2013.01); *B25J 13/02* (2013.01); *B25J 19/005* (2013.01)

(58) Field of Classification Search
CPC . A61B 2046/205; B25J 19/0075; B25J 13/02; B25J 9/126; B25J 19/005
See application file for complete search history.

(56) References Cited

U.S. PATENT DOCUMENTS

| | | | |
|---|---|---|---|
| 3,542,019 A | 11/1970 | Gittins | |
| 3,881,476 A | 5/1975 | Bolker et al. | |
| 4,119,093 A | 10/1978 | Goodman | |
| 4,384,573 A | 5/1983 | Elliott | |
| 4,596,245 A | 6/1986 | Morris | |
| 4,730,609 A * | 3/1988 | McConnell | A61B 46/00 128/853 |
| 4,807,618 A | 2/1989 | Auchinleck et al. | |
| 4,889,136 A | 12/1989 | Hanssen | |
| 5,979,450 A | 11/1999 | Baker et al. | |
| 6,035,228 A | 3/2000 | Yanof et al. | |
| 6,244,268 B1 | 6/2001 | Annett et al. | |
| 6,298,855 B1 | 10/2001 | Baird | |
| 6,315,718 B1 | 11/2001 | Sharratt | |
| 6,382,211 B1 | 5/2002 | Crook | |
| 7,316,233 B2 | 1/2008 | Auerbach | |
| 8,037,884 B2 | 10/2011 | Weinstein et al. | |
| 8,413,660 B2 | 4/2013 | Weinstein et al. | |
| 8,584,281 B2 | 11/2013 | Diel et al. | |
| 10,743,956 B2 | 8/2020 | Pecora | |
| 11,129,765 B2 * | 9/2021 | DeSilets | A61B 46/40 |
| 2007/0282311 A1 | 12/2007 | Scott et al. | |
| 2010/0178100 A1 | 7/2010 | Fricke et al. | |
| 2010/0192960 A1 | 8/2010 | Rotolo | |
| 2012/0065475 A1 | 3/2012 | Hill et al. | |
| 2015/0065839 A1 | 3/2015 | Farah et al. | |
| 2016/0008072 A1 | 1/2016 | Pecora | |
| 2016/0228315 A1 | 8/2016 | Perlman et al. | |
| 2018/0289439 A1 | 10/2018 | McGahan | |

FOREIGN PATENT DOCUMENTS

| | | |
|---|---|---|
| EP | 2722029 A2 | 4/2014 |
| WO | 2017147350 A1 | 8/2017 |
| WO | 2018004531 A1 | 1/2018 |

OTHER PUBLICATIONS

Extended European Search Report dated Jan. 29, 2021 for EP Patent Application No. 18787211.4.

\* cited by examiner

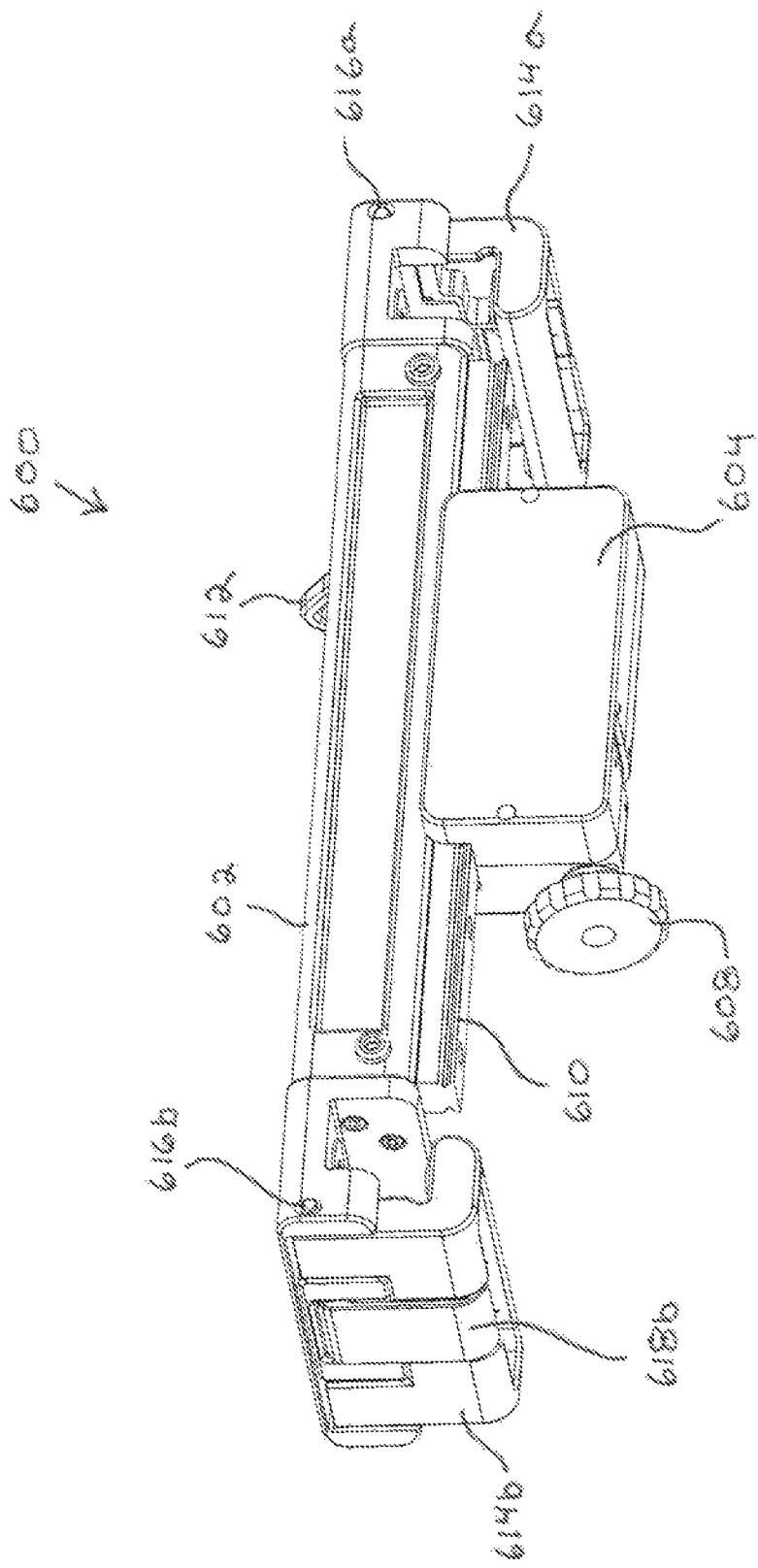

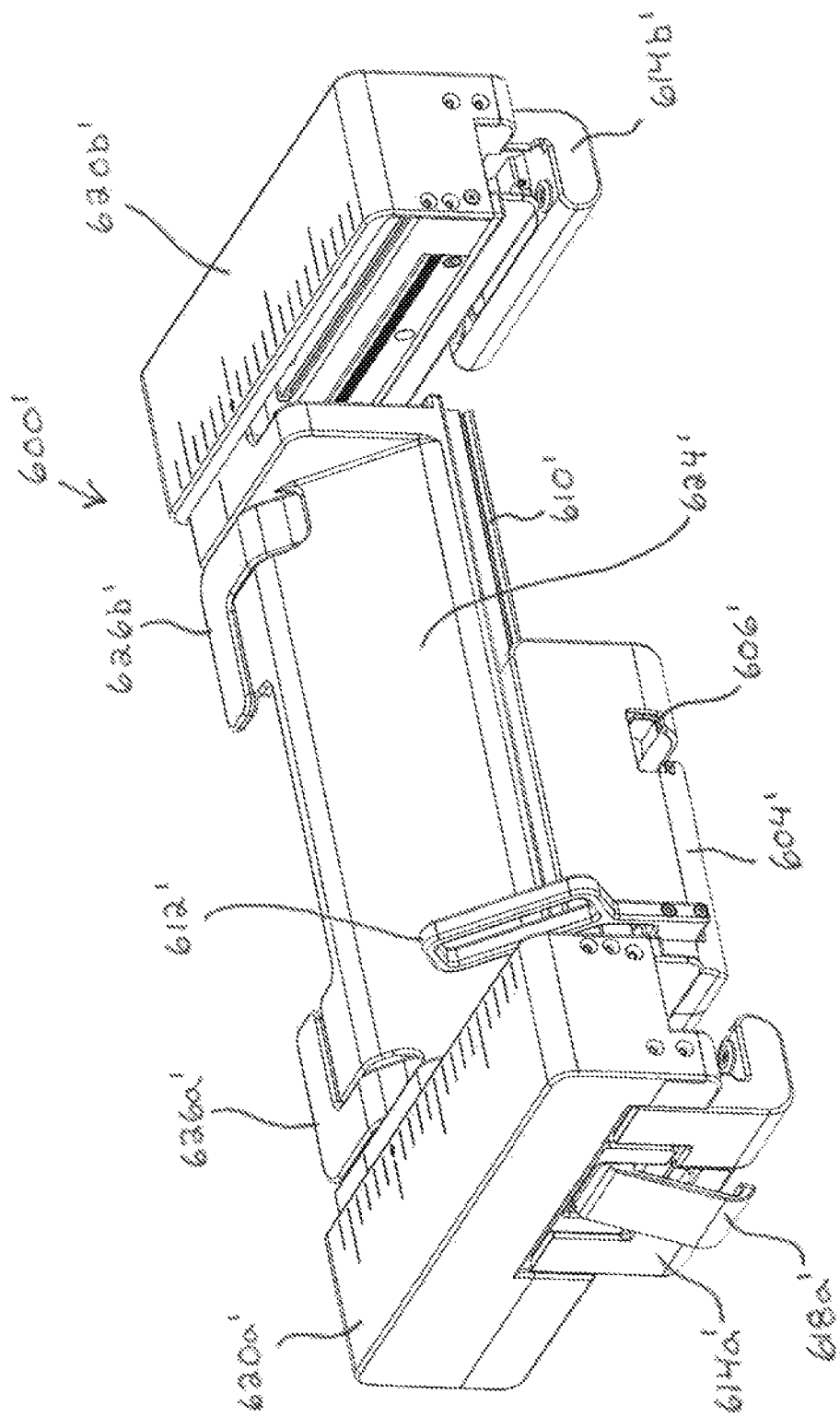

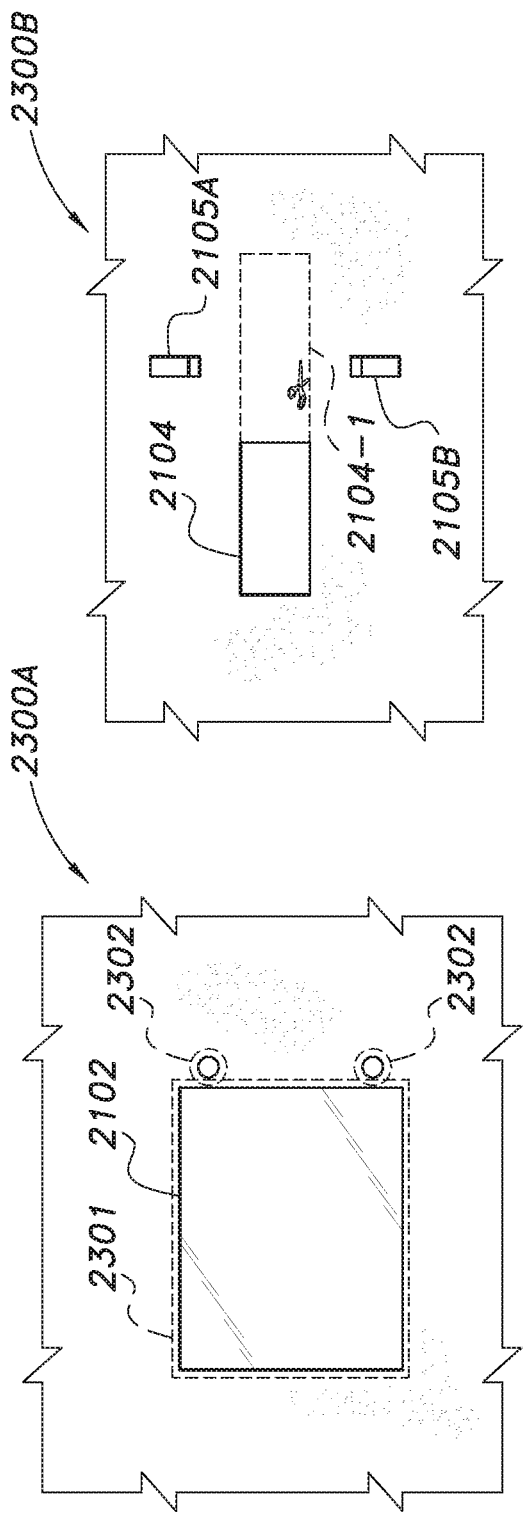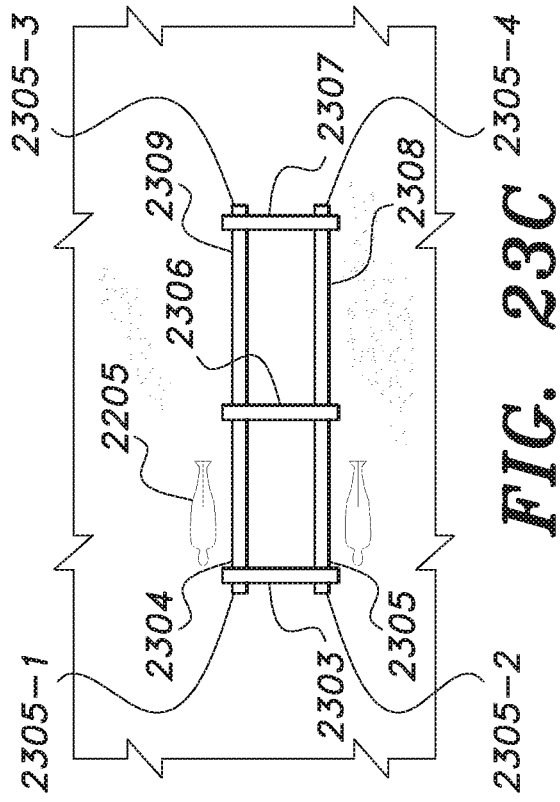
FIG. 23A
FIG. 23B
FIG. 23C

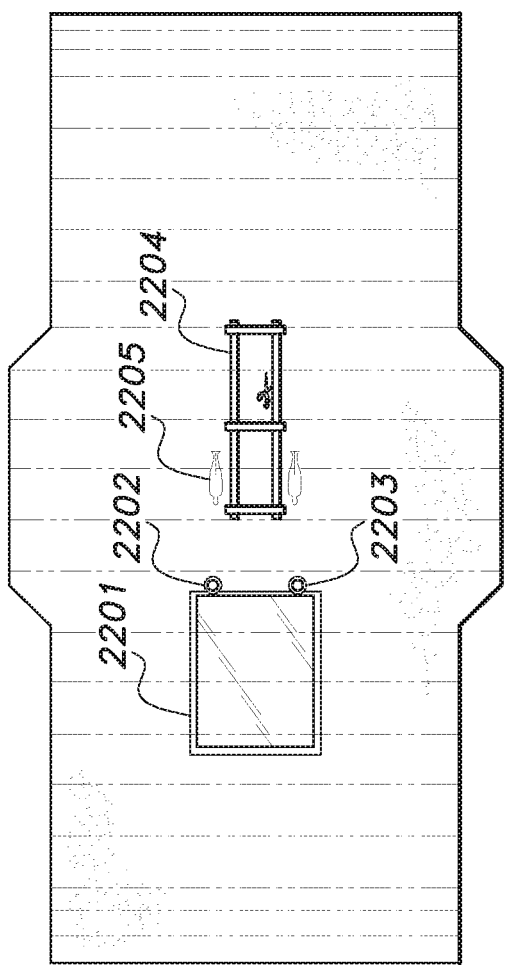
FIG. 25
FIG. 26

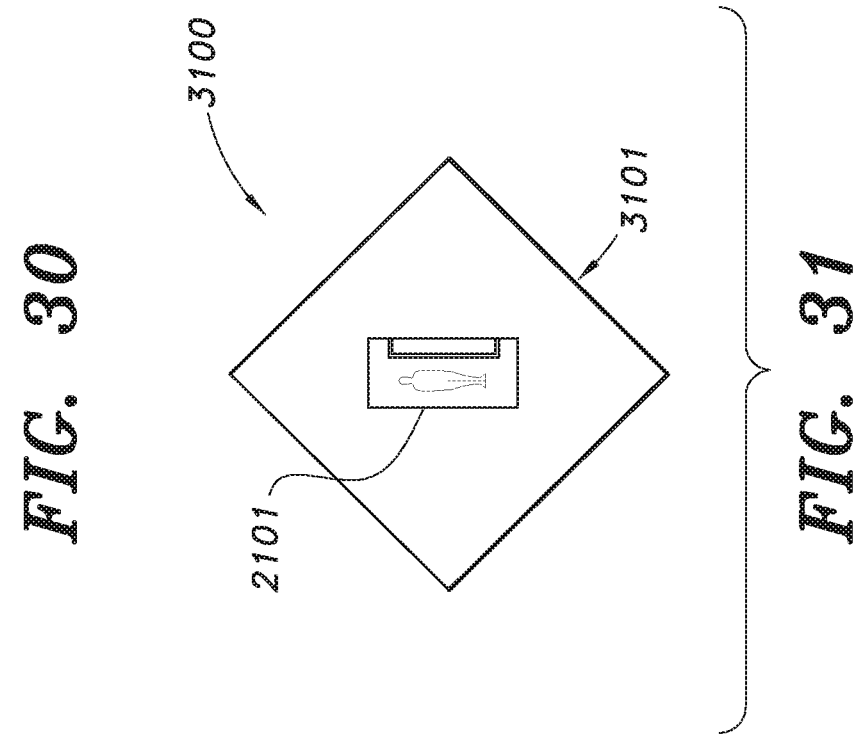

SYSTEM, APPARATUS AND METHOD FOR PATIENT POSITIONING PRIOR TO, DURING AND/OR AFTER MEDICAL PROCEDURES

CROSS-REFERENCE TO RELATED APPLICATION

The present application is a continuation of U.S. patent application Ser. No. 15/912,530, filed Mar. 5, 2018, which is a continuation-in-part of U.S. patent application Ser. No. 15/493,700 filed Apr. 21, 2017, now U.S. Pat. No. 10,905,614, the subject matter of which is incorporated by reference in its entirety.

BACKGROUND

Properly positioning or repositioning a patient prior to and during medical procedures can be important. For example, in cervical surgery, precise, convenient and repeatable positioning of the patient's head and neck is helpful to enable access to the surgical site. It is desirable if the surgeon or other healthcare professional is able to fix the precise position of the patient, and also, when appropriate, change the position to a different fixed position. Prior art surgical tables or equipment often place patients in positions that are not physiologically or ergonomically optimal. Position-related complications can be severe if the head and neck position are not proper.

During a medical procedure, the surgeon would generally prefer to avoid moving through positions that strain the patient, such as placing undue tension or compression on the spine, or that could otherwise cause complications. It can be beneficial to quickly and conveniently reposition the patient to limit the time under anesthesia and other complications associated with a prolonged procedure. Such quick and convenient reposition of the patient can also be beneficial to the medical team, thereby reducing fatigue and avoiding unnecessary distractions. It is desirable if all repositioning can be done without compromising the sterile nature of the procedure. If the surgeon or other personnel are forced to access areas behind the surgical drape (e.g., to reposition the patient), resterilization is required. This prolongs the procedure and introduces risks of compromising the sterile nature of the procedure.

The prior art includes various mechanical mechanisms for supporting a patient's head and neck during a cervical procedure. Certain pre-existing positioning devices have multiple adjustments or knobs that require several members of the surgical team to position or reposition the patient. In use, one individual is required to hold or otherwise support the patient's head, while at least a second individual is required to manually loosen and tighten the knobs. This can be a time-consuming and tedious way to achieve satisfactory positioning.

During position or repositioning of the patient, the relatively long time period required for the surgeon or medical staff to support the weight of the patient is not ideal. When initially attaching existing prior art system or arms to the patient's head in a skull clamp, certain systems require four separate knobs that must be turned and fully seated. This can take anywhere from fifteen to forty-five seconds, and the surgeon or medical team member is often leaning or moving in non-ergonomic or uncomfortable positions during this process. Adjusting the patient's head orientation with prior art system or arms usually entails releasing two or three of the axes, repositioning, then retightening. This process can take approximately thirty seconds, all this time while the physician must hold the patient's head fixed. Given the relatively long time period to complete the above-described steps, these portion of the surgery or pre-surgery can be challenging for the medical team.

One specific example of a prior art device is the MAYFIELD® Ultra 360™ Patient Positioning System (the "Mayfield"). The Mayfield has independent, rotating and self-locking handles, and two double-cam action locking handles for easier opening and closing for secure, quick fixation. Another specific example of a prior art system for supporting and positioning a part of a patient's body is the Allen Medical Systems, Inc. C-Flex® design described in U.S. Pat. No. 8,413,660 ("the '660 patent"), the disclosure of which is hereby incorporated by reference in its entirety. The device of the '660 patent includes at least two joints, each of which has a locked state and an unlocked state, and a release system for allowing an operator, such as a surgeon, to select between the locked state and the unlocked state. The release system of the '660 patent has an operator control interface remote from the joints and at a location that enables the operator to support the weight of the body part while at least one of the joints is in the unlocked state.

The above-described conventional devices have several limitations. For example, fully mechanical devices require or result in relatively abrupt movements of the patient prior to or during surgery. The prior art devices often require the surgeon or other medical personnel to "break scrubs" by entering or accessing an area behind or beneath the surgical drape. Some of these devices allow adjustability in only discrete increments, rather than offering a continuous spectrum of adjustability. The discrete adjustability can result in suboptimal positioning.

In the case of the '660 patent, the ball pivot 166 is located proximate to the device's joint linkages, near the mounting to the surgical table, which is a relatively far distance from the patient's head, thereby causing delicate or relatively minor movements of the patient's head to be more challenging. Other movements of the system of the '660 patent require unlocking of thumbscrews that are remote from the corresponding joint. Therefore, patent positioning and repositioning of the '660 patent often requires multiple people and potential compromise of the sterile nature of the procedure. In addition, in an unlocked state, movement of the arm of the '660 patent is not particularly smooth. The system of the '660 patent has a relatively high stiction to start each motion, which causes movement of the patient to be jerky.

SUMMARY

In one embodiment, the presently disclosed technology is directed to a system for positioning a patient before, during or after a medical procedure. The system can include an arm assembly having a proximal end, an opposing distal end, and at least one joint therebetween. The joint can be configured to permit the distal end of the arm assembly to move with respect to the proximal end of the arm assembly. The proximal end of the arm assembly can be configured to be fixed with respect to a surgical table. The system can also include a ball joint mechanism attached to (i) the distal end of the arm assembly and (ii) a head support configured to support a patient's head. The ball joint mechanism can include a ball joint and a motor. Activation of the motor can permit or prevent rotation of the ball joint In another embodiment, the presently disclosed technology is directed to a system for positioning a patient before, during or after a medical procedure. The system can include a surgical table, a base removably attachable to the surgical table, and a head support configured to contact the patient's head. At least a portion of the head support can include at least one exposed electrical contact. The system can also include an arm assembly having a proximal end, an opposing distal end, at least three spaced-apart joints therebetween, and at least two arm links that attach the joints. Each joint can be configured to permit the distal end of the arm assembly to move with respect to the proximal end of the arm assembly. The proximal end of the arm assembly can be configured to be fixed with respect to the base attached to the surgical table. At least one of the two arm links can include at least one battery. The system can also include a ball joint mechanism attached to (i) the distal end of the arm assembly and (ii) the head support. The ball joint mechanism can include a ball joint and a motor. Activation of the motor can permit or prevent movement of the ball joint.

In yet another embodiment, the presently disclosed technology is directed to a system for positioning a patient before, during or after a medical procedure. The system can include a base having a first body and a second body. The first body can be attachable to a surgical table and movable with respect to the surgical table along a first axis. The second body can be movable with respect to the first body in a direction perpendicular to the first axis. The system can also include an arm assembly having a proximal end, an opposing distal end, and at least one joint therebetween. The joint can be configured to permit the distal end of the arm assembly to move with respect to the proximal end of the arm assembly. At least a portion of the proximal end of the arm assembly can be inserted into the first body of the base and fixed thereto.

In an example embodiment of the surgical drape, the surgical drape may include a top surface and an opposite bottom surface, one or more transparent windows on the top surface of the drape, one or more openings on the top surface of the drape, one or more fastener components, and one or more covers on the top surface of the drape, the one or more covers extending perpendicularly upward from the top surface of the drape. The one or more covers configured to receive control handles of a surgical device.

The one or more covers may include a first segment that extends above the top surface of the drape; and a second segment that includes a flange of a respective cover. The flange may be below the top surface of the drape. Further, in an example embodiment the covers may include one or more fastener components. The annular ring may include adhesive tape and create a bond between the bottom surface of the drape and the flange.

According to an example embodiment of the surgical drape, the drape may be folded in an accordion fashion such that proximal end and distal end of the drape is folded inward toward a center of the drape. Additionally, the drape may be folded orthogonally in both lateral directions, bending each side inward medially. The method of folding may further include identifying a first marking on the proximal most end of the drape prior to the folding of the proximal most end; and identifying a different second marking on the distal most end of the drape prior to the folding of the distal most end. Further, the drape may be inserted in a package.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings various illustrative embodiments. It should be understood, however, that the invention is not limited to the precise arrangements and instrumentalities shown. In the drawings:

FIG. 13A is another perspective view of the component shown in FIG. 12.

FIG. 14 is a perspective view of another embodiment of the component shown in FIG. 11.

FIG. 23A illustrates a top view of an embodiment of the transparent window placed on the top side of the surgical drape and a representation of different liners underneath the transparent window on the bottom side of the surgical drape.

FIG. 23B illustrates a top view of an embodiment of an extendable opening positioned on the top side of the surgical drape.

FIG. 23C illustrates a bottom view of an embodiment of the tape configuration along with markings on the bottom side of the surgical drape.

FIG. 25 illustrates an embodiment of a bottom side of the surgical drape depicting the accordion style fold lines.

FIG. 26 illustrates an embodiment of side view of FIG. 25 depicting the partial accordion fold of the surgical drape.

FIG. 27 illustrates an embodiment of complete accordion folded configuration of the surgical drape of FIG. 21 along an axis parallel to the top surface of the surgical drape.

FIG. 28 illustrates a side view of FIG. 27.

FIG. 29 illustrates an embodiment of each side of the complete accordion folded drape that is folded back towards the middle.

FIG. 30 illustrates an end view of an embodiment of the final folded configuration.

FIG. 31 illustrates a view of an embodiment of the surgical drape as folded in orthogonal fashion as shown in FIG. 30 placed on a protective wrap.

DETAILED DESCRIPTION

Figure 1:
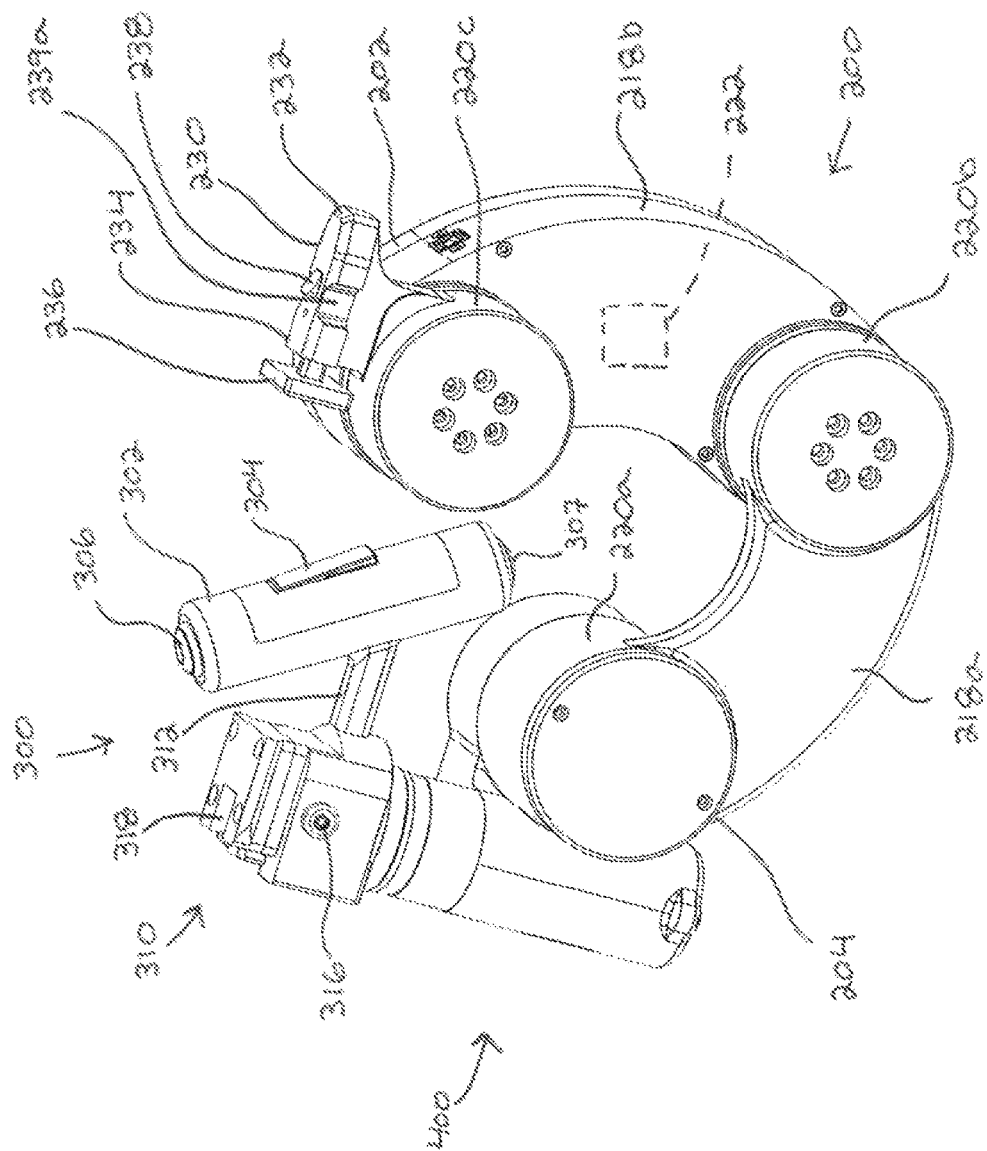
FIG. 1 is a perspective view of at least a portion of a system or apparatus according to an embodiment of the present disclosure.

While systems, apparatus and methods are described herein by way of examples and embodiments, those skilled in the art recognize that the systems, apparatus and methods of the presently disclosed technology are not limited to the embodiments or drawings described. It should be understood that the drawings and description are not intended to be limited to the particular form disclosed. Rather, the intention covers all modifications, equivalents and alternatives falling within the spirit and scope of the appended claims. Any headings used herein are for organizational purposes only and are not meant to limit the scope of the description or the claims. As used herein, the word "may" is used in a permissive sense (i.e., meaning having the potential to) rather than the mandatory sense (i.e., meaning must). Similarly, the words "include," "including," and "includes" mean including, but not limited to. Unless specifically set forth herein, the terms "a," "an" and "the" are not limited to one element but instead should be read as meaning "at least one." The term "actuator" is broadly defined herein to mean any component capable of at least initiating movement or control of a mechanism or system, and includes a trigger, a button, a switch or any other enabling device. The terminology includes the words noted above, derivatives thereof and words of similar import.

Referring to the drawings in detail, wherein like numerals indicate like elements throughout, one embodiment of the presently disclosed technology is directed to a modular, multi-component system, apparatus and method that allows a surgeon and/or a medical team to position and reposition a patient before, during and/or after surgery though electrical and/or mechanical means. As compared to the prior art, the cervical management system of one embodiment of the presently disclosed technology increases both the speed at which a patient can be positioned and repositioned in a desirable configuration and the reliability that the desired configuration will be achieved. The term "patient" is broadly defined herein to include human patients of all sizes, genders and demographics, as well as animals (e.g., for veterinarian purposes).

The presently disclosed technology allows a single surgeon or a single healthcare professional, as opposed to a team of two or more, to make inter-operative (e.g., both preoperative and postoperative) adjustments to the patient without having to "break scrubs." As a result, more efficient and effective surgeries should result. The system or apparatus, generally designed 100, of the presently disclosed technology includes components with specific motion ranges and adjustment capabilities that can be combined in different ways to address different clinical needs for (i) simple or complex procedures (for example, but not limited to, cervical procedures and neurosurgery), (ii) intra-operative adjustment, (iii) small or large adjustment ranges, and/or (iv) prone positioning for cervical and/or thoracic/lumbar. The system or apparatus, therefore, can enable precise, smooth and continuous movement without "jerking" or any sudden movements. The system or apparatus 100 can support movement of the patient in all degrees of freedom (i.e., lateral, longitudinal, vertical, yaw, pitch and role). The system or apparatus can provide optimized sagittal motion range, floating lateral and longitudinal motion to allow for low force compensation during head adjustment, FIGS. 1-7 and 16-18 show embodiments of an arm assembly, generally designated 200, a ball joint mechanism, generally designated 400, and a first operator control interface, generally designated 300, of the presently disclosed technology. In one embodiment, the arm assembly 200, the ball joint mechanism 400, and the first operator control interface 300 can be permanently or non-removably attached. In another embodiment, one or more of these components can be removably attached to one another to create a modular system of interchangeable parts. As described in detail below, at least a portion of the arm assembly 200 can pivot, spin and/or rotate with respect to at least a portion of the ball joint mechanism 400, and at least a portion of the ball joint mechanism 400 can pivot, spin and/or rotate with respect to at least a portion of the first operator control interface 300. Such relative movement of these components gives the surgeon and other healthcare professional(s) increased control of the patient's positioning prior to, during and/or after surgery, and contributes to the overall effectiveness and functionality of the system, apparatus and method of the presently disclosed technology.

As shown in FIGS. 1-4, 7 and 16-18, the arm assembly 200 can include a proximal end 202 and an opposing distal end 204. One or more spaced-apart rotary joints 220a, 220b, 220c can be located between the ends 202, 204. One or more of the joints 220a, 220b, 220c can be pivot joints. In one embodiment, when making an analogy to a human arm, the first or proximal-most joint 220c can function as a shoulder joint; the second or mid-joint 220b can function as an elbow joint; the third or distal-most joint 220a can function as a wrist joint. One or more link arms 218a, 218b can be connected by one or more of the joints 220b. The presently disclosed technology can employ an arm assembly 200 with more than three rotary joints (or joints of any type) and more than two arm links as shown herein, if such additional motion or dexterity would be beneficial to the surgeon or other healthcare professional.

Each joint 220a, 220b, 220c can be configured to permit the distal end 204 of the arm assembly 200 to move with respect to the proximal end 202 of the arm assembly 200. At least a portion of the proximal end 202 of the arm assembly 200 can be coupled (directly or indirectly) and/or removably or permanently fixed (directly or indirectly) with respect to a support apparatus 150, such as a surgical table. At least a portion of the distal end 204 of the arm assembly 200 can be configured to be coupled (directly or indirectly) and/or removably or permanently fixed (directly or indirectly) to one or more devices, such as a device configured to support a patient's head. In one embodiment, one or more batteries 222 or other power source(s) can be enclosed within one or more of the link arms 218a, 218b, and operatively connection (e.g., through wires) to one or more components of the system 100 that require electrical power. The batteries 222 can be a convenience by allowing the system to be wireless. The batteries 222 can be rechargeable.

As mentioned, one problem with conventional head positioning devices is that the weight of the patient's head and neck, combined with the weight of the positioning apparatus, can make it difficult for the surgeon to safely support the patient's anatomy at the instant the joints release. To address this limitation, the release of the rotary joints 220a, 220b, 220c and the ball joint mechanism 400 can be safety-enabled to prevent accidental unlocking. In addition, one or more of the joints 220a, 220b, 220c can include a motion damping mechanism, which, when one or more of the joints 220a, 220b, 220c are in an unlocked state, provides an appropriate inertia opposing any acceleration of the joints 220a, 220b, 220c and thereby minimize unwanted motion of the patient's head and/or neck.

Figure 3:
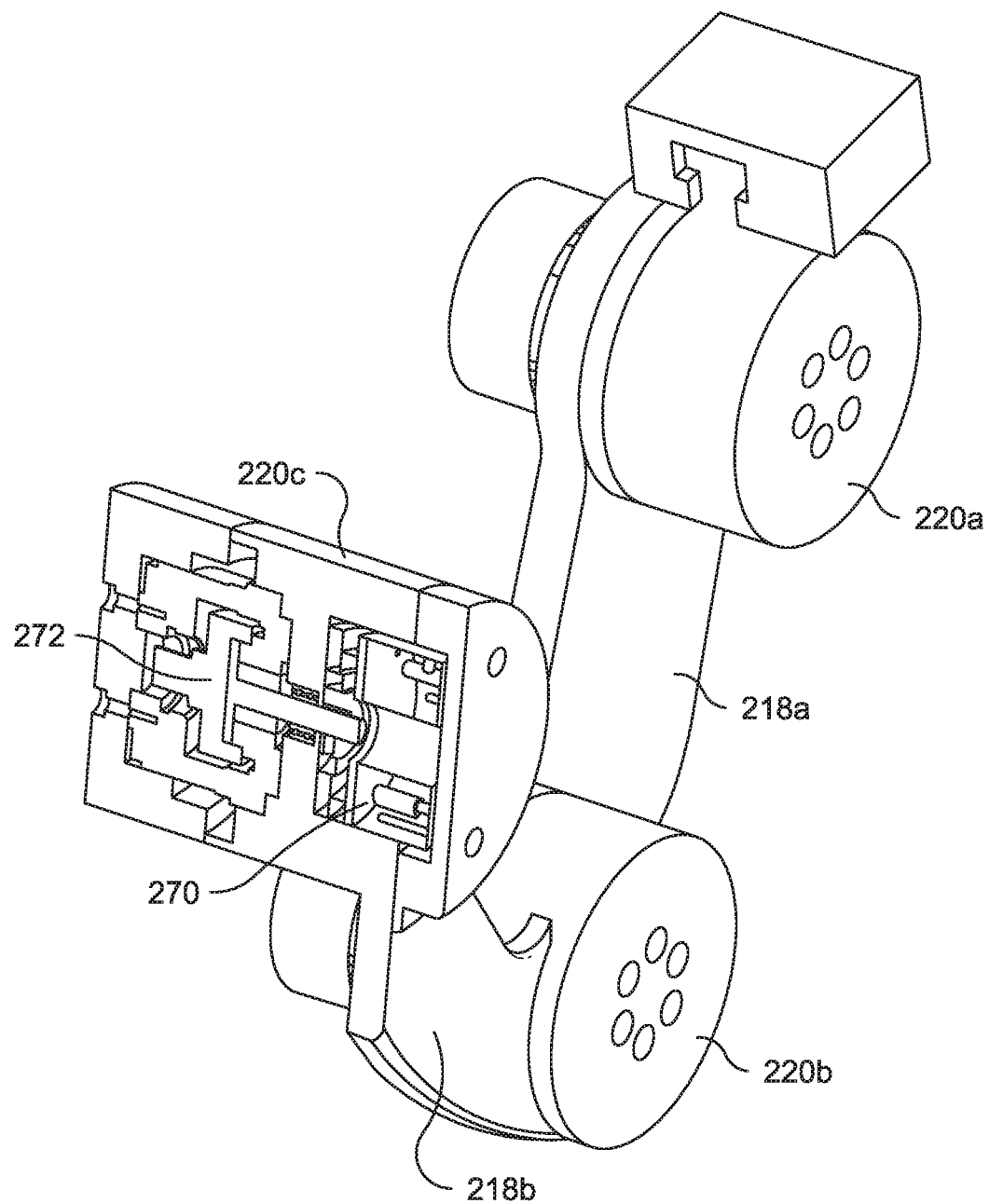
FIG. 3 is a perspective view of an embodiment of a component of the structure shown in FIGS. 1 and 2, wherein a segment of the component is shown in cross-section taken along line 3-3 of FIG. 2.
Figure 4:
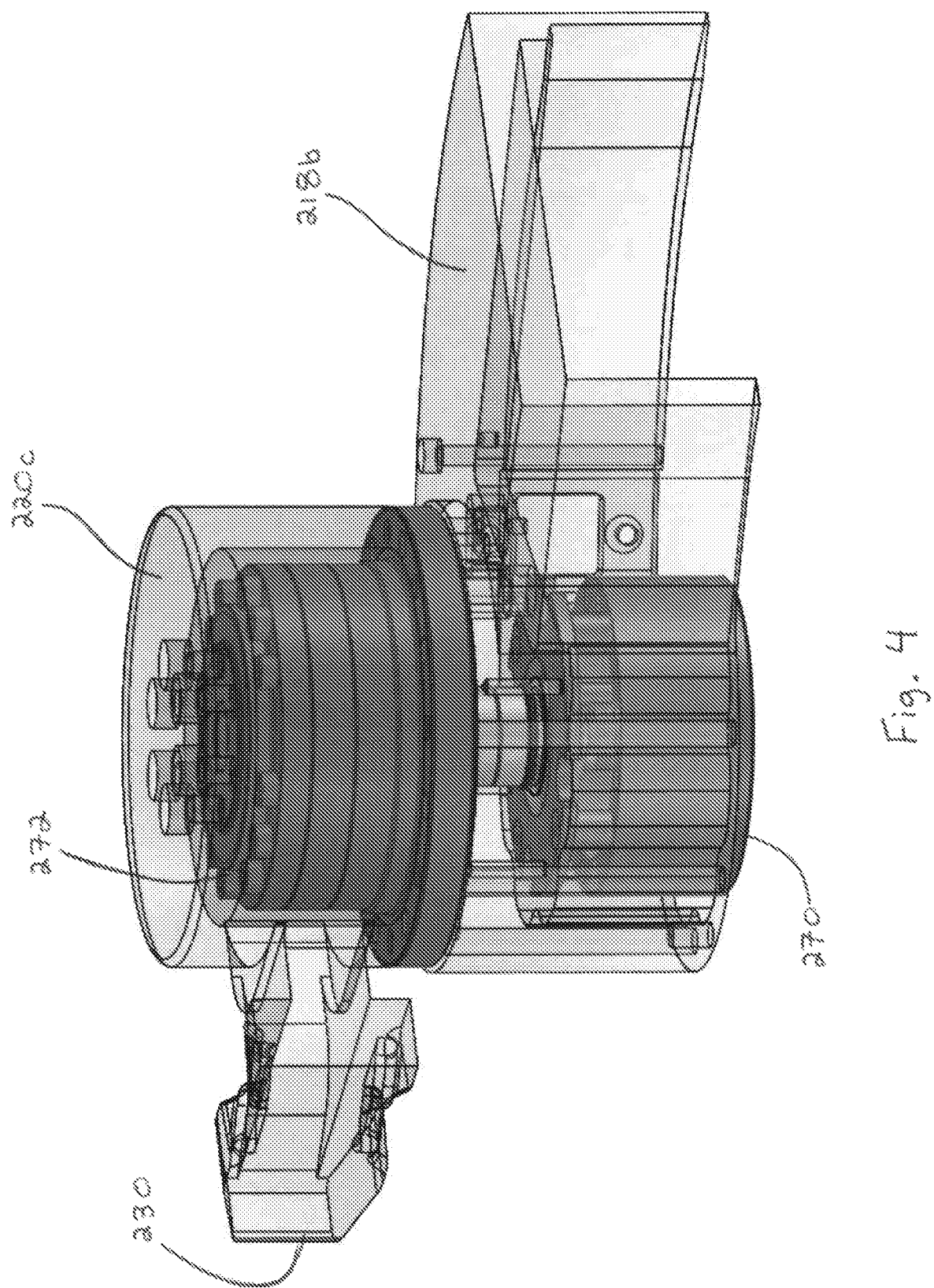
FIG. 4 is a perspective view of at least a portion of the component shown in FIG. 3; wherein a segment of the component is shown as partially transparent for clarity.

In particular, referring to FIGS. 3 and 4, one or more of the joints 220a, 220b, 220c can include at least one brake 270 operatively connected to at least one gear or gear train 272. Each brake 270 can be an electro-mechanical or an electro-magnetic fail safe brake, and each gear 272 can be a high ratio harmonic gear drive, strain wave, planetary, or other type gear box. The gear(s) 272 are not limited to the above type or configuration, as one or more could be other types of gears, such as planetary or cycloidal or even direct drive (no gearing whatsoever). Each gear box 272 can reflect or produce the brake rotor inertia to the user (e.g. surgeon), multiplied by the square of the gear ratio to provide inertial dampening. This damping can prevent sudden dropping of the patient's head, for example, when the joint release mechanism is engaged or when one or more of the operator control interfaces are released by the surgeon or other healthcare professional. One or more of the joints 220a, 220b, 220c can include additional features or components to add in the functionality of the system. For example, an encoder can be positioned at or in one or more of the joints 220a, 220b, 220c to aid the medical team's ability to return the arm assembly 200 and/or the entire system to a desired or original position. One or more counterbalance springs and/or motors can be employed on or in one or more of the joints 220a, 220b, 220c to provide a gravity assist and/or active positioning.

In one embodiment, the higher the ratio of the gear box(es) 272, the smaller the brake(s) 270 can be to accomplish the desired functionality. Furthermore, the timing of the release of one or more of the joints 220a, 220b, 220c and/or the ball joint mechanism 400 could be staggered such that the weight of the patients head and neck is progressively transferred from the device to the operator, allowing the surgeon time to react to any sudden drop of the patient's head. One or more torsional or other spring type can be operatively connected to the joint or gear(s) 272 that could provide a gravity compensation torque, further reducing the possibility of sudden acceleration of the patient's head and neck The rotary joints 220a, 220b, 220c and ball joint mechanism 400 can be configured to lock in any precise, desired head posture and to not drift while locking. The brake(s) 270 and/or a motor (described in detail below) of the ball joint mechanism 400 can lock quickly (e.g., measured in milliseconds) so that there is no need for the surgeon or other healthcare professional to hold the patient's head still for an extended period of time (which is required by prior art devices).

One or more of the batteries 222 can supply power to each brake 270 and/or motor (described in detail below) of the ball joint mechanism 400. The present disclosure is not limited to batteries as the sole power source for these or other electrical components of the system, as other well-known power sources can be used. For example, the system or any portion thereof could plug directly into the surgical table (supplied with power) or a wall outlet to get its power. As described in detail below, one or more operator control interfaces are operatively and/or electrically coupled to each brake 270, each motor, and/or each battery 222 or other power source. In one embodiment, upon activation of one or more of the operator control interfaces, electrical power can be supplied to one or more of the brakes 270 and/or motor(s).

In one embodiment, one or more of the brakes 270 and motor(s) are configured to be "fail safe." Thus, when power is removed from the brakes 270 and/or motor(s), one or more of the link arms 218a, 218b and/or the ball joint mechanism 400 can fully lock-up, which is the normal state during surgery. When power is applied (via the enable and/or release buttons described herein), the brakes 270 and/or motor(s) are free to rotate. Additional motors and servos could be added to provide any amount of holding or drive torque. In an alternative embodiment, one or more brakes, motors or other components can apply variable friction to one or more of the link arms 218a, 218b and/or the ball joint mechanism 400, thereby slowing movement of these components.

The above-described arrangement and features allow one or more of the joints 220a, 220b, 220c and/or each ball joint mechanism 400 to have an unlocked state and a locked state. In the unlocked stated, each joint 220a, 220b, 220c and each ball joint mechanism 400 can be freely moveable without any or only negligible resistance. This can allow for maximum manipulation or maneuverability of the entire system. In the locked state, each joint 220a, 220b, 220c and each ball joint mechanism 400 can be fixed, thereby providing maximum support and/or stability to the patient. Of course, not all of the joints 220a, 220b, 220c or the ball joint mechanism 400 are required to be locked or unlocked at the same time. For example, one or more of the joints 220a, 220b, 220c and/or ball joint mechanism 400 can be unlocked, while one or more of the remaining joints 220a, 220b, 220c or ball joint mechanism 400 can be locked. Such a configuration allows for some or more finite movement or manipulation of the system.

Figure 2:
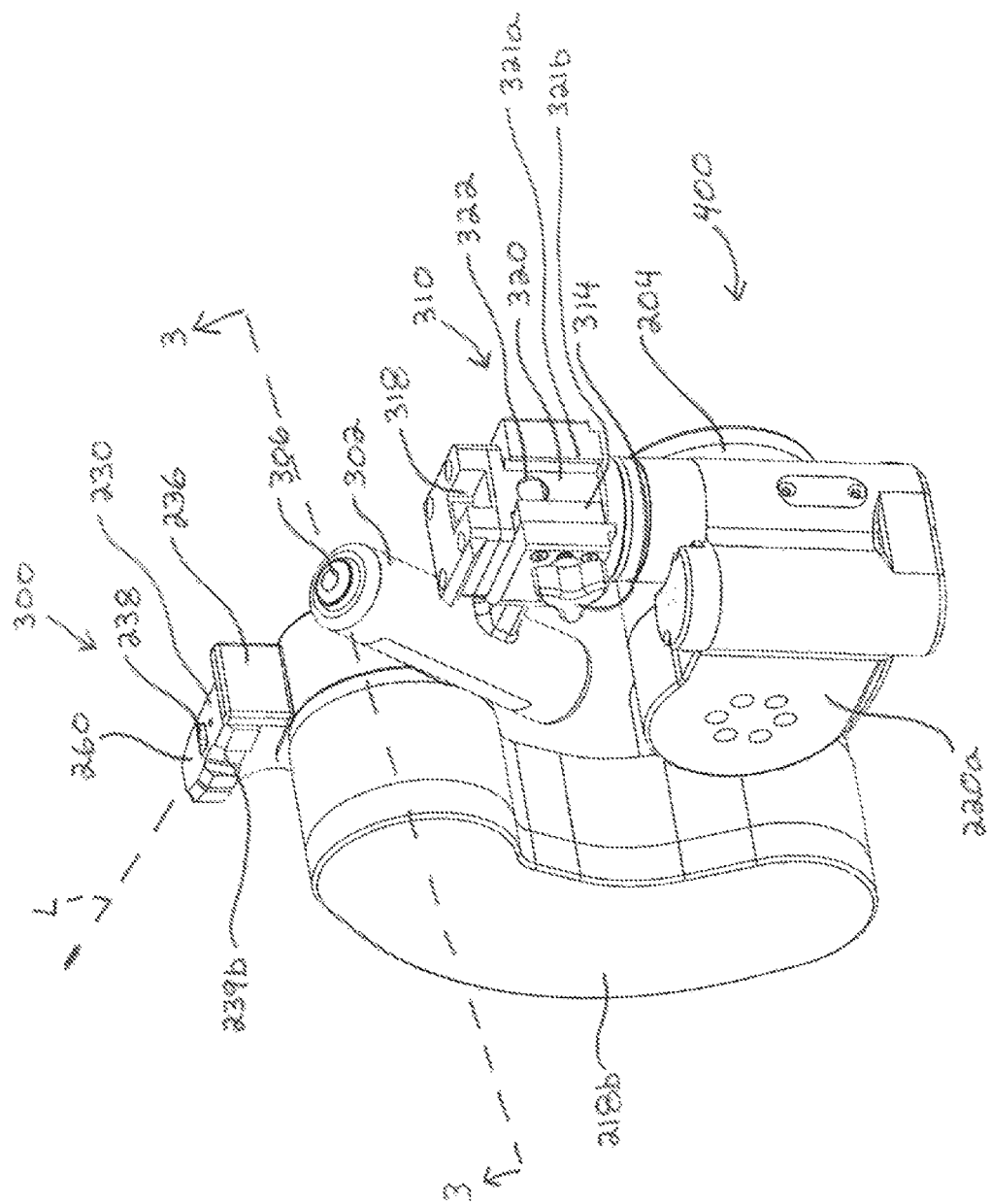
FIG. 2 is another perspective view of the structure shown in FIG. 1.

As shown in FIGS. 1 and 2, a first mount or quick connection 230 can be located at or proximate to the proximal end 202 of the arm assembly 200. The first mount 230 can include a body 260 having a longitudinal axis L (see FIG. 2) that can extend in a plane defined by the link arms 218a, 218b. At least a portion of the first mount 230 can be sized, shaped and/or configured to fit into and/or be received by a recess or receptacle of a base (embodiments described in detail below), for example, that attaches to a surgical table. In one embodiment, the first mount 230 can be fixedly or permanently attached to the proximal-most rotary joint 220c. The proximal-most link arm 218b can rotate about the first mount 230 as a result of the proximal-most rotary joint 220c. A distal end 232 of the first mount 230 can include a tapered portion to facilitate easy insertion into the recess or receptacle. An opposing proximal end 234 can include a spring-biased tab or button 236. Depression of the button 236 can retract a projection 238 biased outwardly from the first mount 230, which can facilitate removal of the first mount 230 from the recess or receptacle. Opposing sides of the first mount 230 can include grooves or cut-outs 239a, 239b designed to mate with or complement portions of the recess or receptacle.

Figure 5:
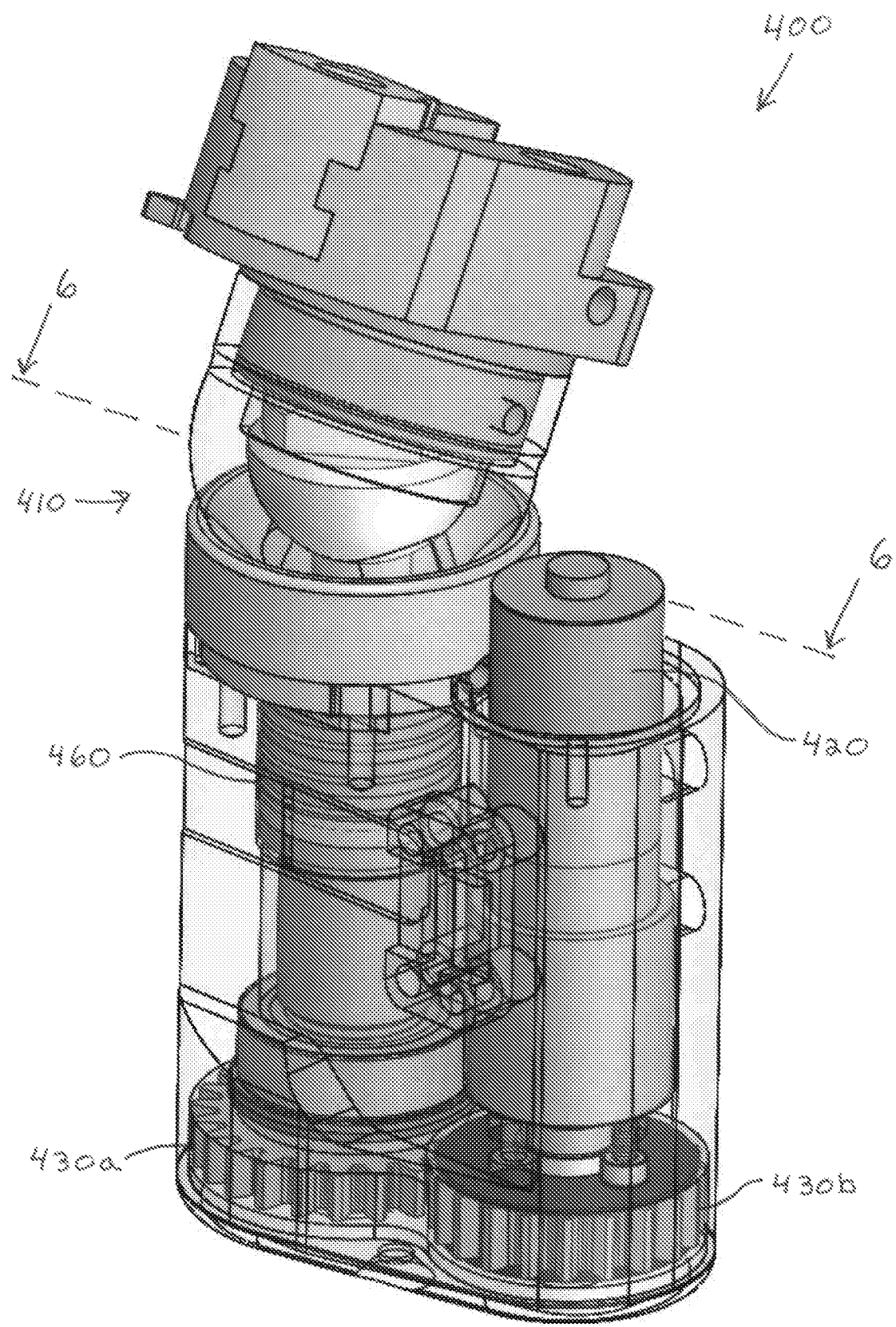
FIG. 5 is a perspective view of an embodiment of another component of the structure shown in FIG. 1, wherein segments of the component are shown as partially transparent for clarity.
Figure 6:
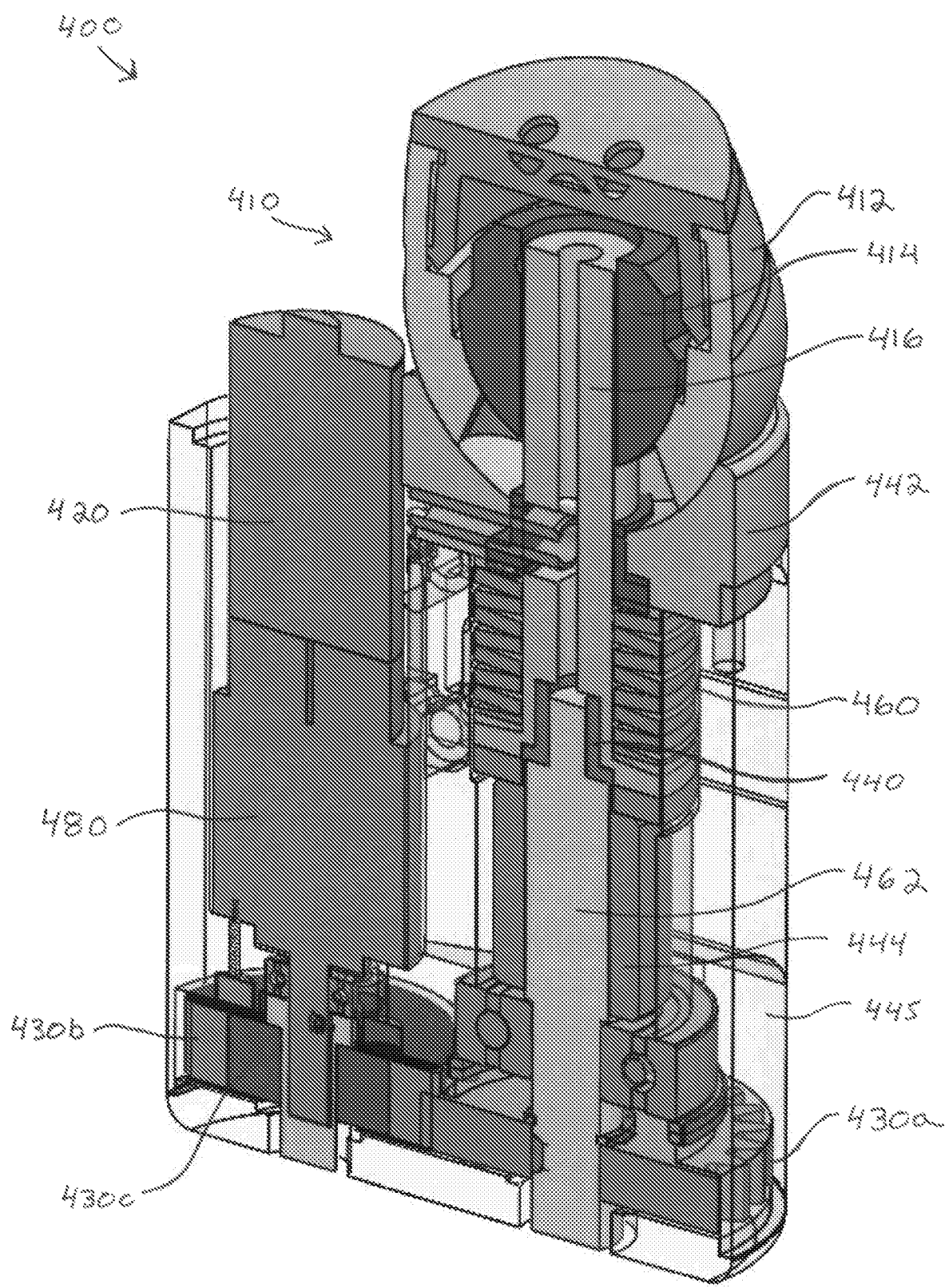
FIG. 6 is a cross-sectional perspective view of the component shown in FIG. 5, taken along line 6-6 of FIG. 5.
Figure 7:
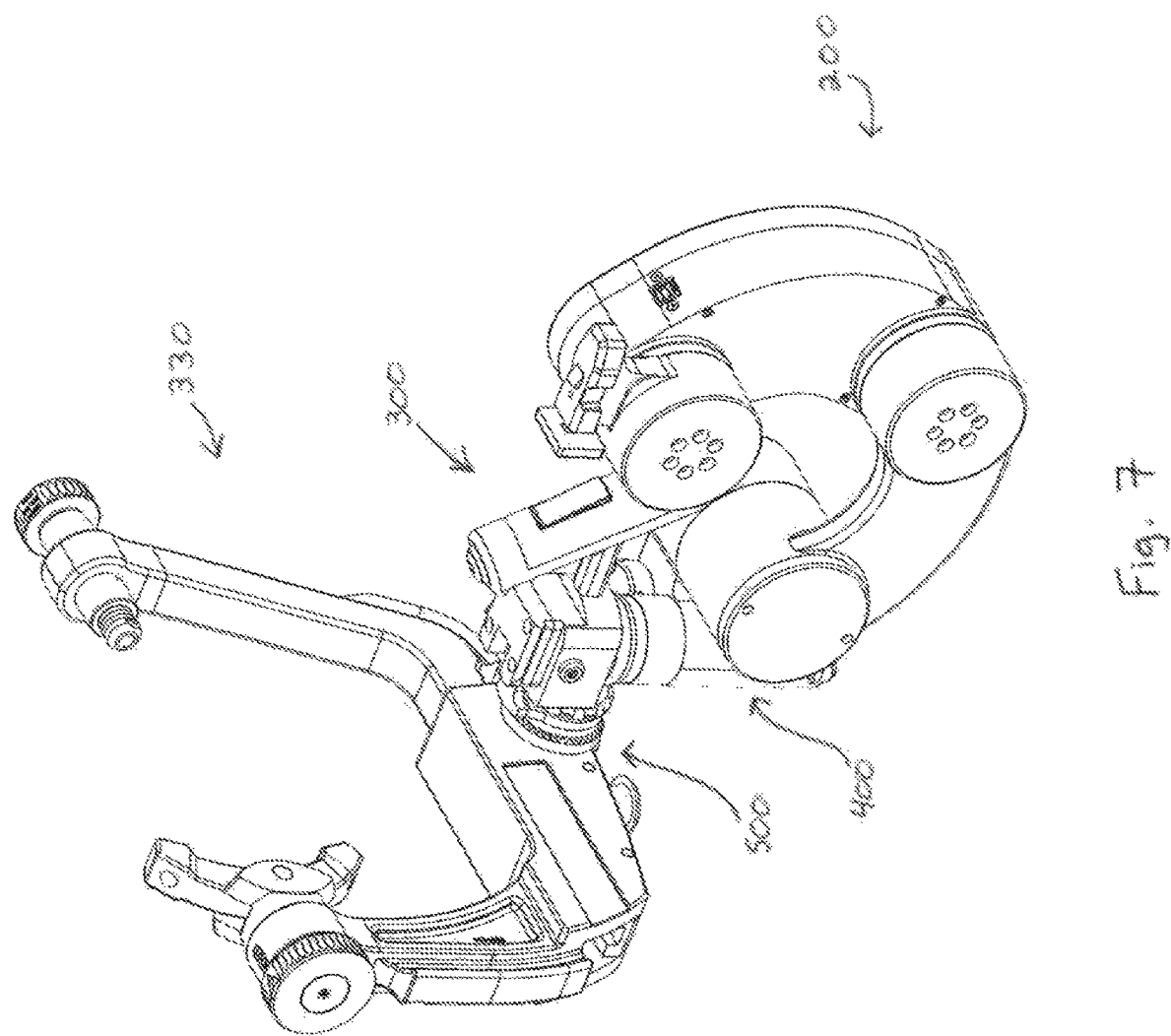
FIG. 7 is another perspective view of the structure shown in FIG. 1, wherein the structure is shown attached to an embodiment of yet another component of the presently disclosed technology.

FIGS. 5 and 6 show detailed views of one embodiment of the ball joint mechanism 400 of the presently disclosed technology. The ball joint mechanism 400 can include at least one ball joint 410 operatively connected to at least one motor 420, such as a DC brush motor. The motor 420 can be operatively connected to one or more of the batteries 220 and can be activated by one or more of the operator control interface(s). The ball joint 410 can be a conventional three-degree-of-freedom ball joint allowing rotation in all three axes. The ball joint 410 can include a ball seat 412 and a swivel ball 414. A rod or pin 416, which can be threaded, can extend through at least a portion of each of the ball seat 412 and the swivel ball 414 and into a biasing compression spring pack 460. The biasing compression spring pack 460 can be a stack of spring washers or a spring pack.

An opening in a bottom of the ball seat 412, which the rod 416 passes through, can be a slot, restricting motion in one plane and thus creating a two-degree-of-freedom ball joint. If the ball joint's restricted plane is coincident with the plane the three rotary joints enable motion in, redundancy of motion will be reduced. In one embodiment, because of this slot that can restrict motion of the ball joint 410, the ball joint 410 is only able to make yaw and roll adjustments. In this embodiment, when the surgeon wants to make a sagittal plane (i.e., pitch) adjustment, he/she rotates all three joints 220a, 220b, 220c.

Through a thrust bearing/bushing interface 440, the lower end of the rod 416 can contact or engage, but translate independently of, the upper end of a threaded shaft 462, such as a ball screw or lead screw. The lower flange or shoulder of interface 440 can act as a bushing because threaded shaft 462 can rotate, but the rod 416 does not. The lower flange can act as a thrust bearing limiting motion when the spring pack 460 pushes the rod 416 downwardly. In one embodiment, a bottom end of the threaded shaft 462 can extend into and engage a first gear 430a. The first gear 430a can matingly engage a second gear 430b, which in turn matingly engages a clutch 430c. The clutch 430c can be a one-way bearing or a Sprag type clutch. The clutch 430c is not limited to the exact location shown in FIGS. 5 and 6. For example, the clutch 430c could be moved from proximate the second gear 430b to proximate the opposite first gear 430a. A gear reducer 480 can be attached at one end to the clutch 430c and at an opposing (e.g., upper) end to the motor 420.

The threaded shaft 462 can be or form a portion of a rotatory-to-linear (or vice versa) device. In particular, a cylindrical ball screw nut or lead screw nut 444 (see FIG. 6) can be keyed in the housing 445, enabling the nut 444 to move linearly as the threaded shaft 462 is rotated. The ball screw nut 444 can be positioned directly above a bearing. Rotation of the threaded shaft 462 in one direction (e.g., clockwise) can drive or move the ball screw nut 444 at least slightly upwardly, thereby at least slightly compressing the spring pack 460 and thus driving the rod 416 at least slightly upwardly. Likewise, downward motion of the rod 416 (e.g., driven by the force of the spring pack 460) can cause the ball screw nut 444 to translate or otherwise move at least slightly downward. This motion causes the threaded shaft 462 to "back drive."

Linear motion of the ball screw nut 444 can thus push upwardly on the rod 416. In order to push the rod 416 upwardly, sufficient motor power is needed to compress the spring pack 460. When the motor power is released, the spring pack 460 can push the ball screw nut 444 back downwardly, thereby causing the screw shaft 462 to rotate. The purpose of the clutch 430c is to minimize the amount of friction and inertia that must be overcome. With the clutch aligned properly, the motor and its gearbox do not need to rotate, which assures a quick and safe lock-up of the ball joint 410 of the ball joint mechanism 400.

In one embodiment, the ball joint mechanism 400 can be biased to lock the ball joint 410, thereby preventing movement in either of the two degrees of freedom. More particularly, in one embodiment, with the motor 420 in a relaxed or "off" state, the biasing spring pack 460 can bias the rod 416 downwardly, thereby moving the swivel ball 414 downwardly and into engagement with the ball seat 412. In addition, the biasing spring pack 460 can also push the ball seat 412 into engagement with a cup housing 442 (see FIG. 6) beneath the ball seat 412 and above the biasing spring pack 462. Such engagement can lock the position of ball joint 410 and prevent its rotation. This functionality can help to maintain the system 100 in a desired configuration or position, thereby supporting the patient while the surgeon or other healthcare professional performs the medical procedure. In one embodiment, the patient's head is attached (indirectly) to the ball seat 412, so the above-described configuration and components provide two frictional surfaces, both generating holding torque, thereby creating a dual (concentric) ball joint. The torque is "doubled" because the ball seat 412 is captured and tightly clamped on both its inner (e.g., upper) and opposing outer (e.g., lower) ball surfaces.

When it is desirable to reposition the patient, power can be supplied to the motor 420, which, in one embodiment, can cause the second gear 430b to rotate via engagement of the clutch 430c. Rotation of the second gear 430b will engage the first gear 430a, thereby causing rotation of the threaded shaft 462. Rotation (e.g., clockwise when viewed from beneath the ball joint mechanism 400) of the threaded shaft 462 can effectuate a change of the biasing spring pack 460 that can release the ball joint 410. For example, in one embodiment, this rotation of the threaded shaft 462 can cause the ball screw nut 444 and the lower end of the spring pack 460 to be moved at least slightly upwardly, thereby at least slightly compressing the spring pack 460, which in turn can release or at least reduce tension or a downward force previously applied to the rod 416. This can permit the rod 416 to move at least slightly upwardly and release the ball joint 410 from a clamp created by compression of the swivel ball 414 onto the ball seat 412 by the rod 416. The clamp can be a double (concentric) surface ball joint clamp.

When the motor 420 is turned "off" or power is cut to the motor 420, torque is no longer applied to the threaded shaft 462. When this occurs, the force of the compressed spring pack 460 pushes the ball screw nut 444 at least slightly downwardly. Since the ball screw nut 444 is keyed, this linear motion causes the threaded shaft 462 to rotate (i.e., back drive). In this embodiment, without the clutch 430c, the entire drivetrain, including the motor 420 would back drive.

Thus, in one embodiment, when the motor 420 is engaged, activated or powered, the rod 416 can permit the swivel ball 414 of the ball joint 410 to move in two degrees of motion, but can prevent the ball joint 410 from moving or rotating in a third degree of motion.

However, when the motor 420 is not engaged, activated or powered, the rod 416 can prevent any motion or rotation of the ball joint 410. In an alternative embodiment, as understood by those skilled in the art, the drive drain and/or components of the ball joint mechanism 400 can be designed such that activation of the motor 420 prevents movement of the ball joint 410 and deactivating the motor 420 permits movement of the ball joint 410.

In one embodiment, the first and second gears 430a, 430b can be omitted from the design. For example, the same or similar functionality could be accomplished with an "inline" design, where the motor 420, the clutch 430c, and the ball screw 462 are all on the same axis. Such a design would eliminate the gear set, if that is desirable, but could double the height of the ball joint mechanism 400 (which could be acceptable in certain circumstances).

As shown in FIGS. 1, 2 and 16-18, the position of the ball joint mechanism 400 and/or the ball joint 410 relative to other components of the system 100 can be advantageous. In one embodiment, the ball joint 410 can be located or positioned proximate to the patient's head, and generally between the patient's head and the arm assembly 200. When attempting to make minute changes to the position of the patient's head, it can be beneficial for the ball joint 410 to be located proximate to the patient's head, because all rotation of the patient's head affects the patient's neck. Specifically, when reorienting the patients head in the coronal plane (yaw), rotating the head about a point located close to the neck will minimize translation of the head in the coronal plane, thus limiting transverse motion of the cervical vertebra. This proximity of the two-degrees of freedom provided by the ball joint 410 allows the surgeon or other healthcare professional to make minute or finite changes in the orientation of the patient's head with minimal effect on the surgical site. In the prior art, any ball joint is spaced-apart from the patient's head, such that all or a majority of any articulating arm is positioned between the patient's head and the ball joint. Such an arrangement in the prior art can limit the effectiveness and range of coronal plane adjustments.

In one embodiment, one important feature of the ball joint 410 and/or the ball joint mechanism 400 is the locking/unlocking function. Locking can be provided by the failsafe spring pack 460, which can be similar to spring packs employed in electro-mechanical brakes, such as those used on the rotary joints 220a, 220, 220c. Once power to the motor 420 is removed, the clutch 430c can allow the ball joint 410 to lock and/or be locked quickly because the inertia and friction of the motor 420 does not need to be back driven, thus enhancing the safety of the system. The motor 420 can provide the unlocking function by rotating the ball screw 462 and compressing the brake(s) 270. Other important features of the ball joint 410 are the concentric locking surfaces, essentially doubling the holding torque, and the pin 416 in the slot, which reduces it to two degree-of-freedom and thereby eliminating the sagittal plane adjustment conflict.

Referring to FIGS. 1 and 2, the first operator control interface 300 can include a body 302 having a first actuator 304 and a second actuator 306. The first and second actuators 304, 306 can be spaced-apart. The first actuator 304 can be in the form of a spring-actuated trigger or tab, which can be depressed and/or engaged by a user when the user grasps the body 302. The second actuator 306 can be in the form a spring-actuated push button, which can be depressed and/or engaged by a user's finger. In operation, when the user grasps the body 302 tightly, enabling actuator 304, he/she is exerting control of the device and is likely to have a strong enough grip to support the weight of the unlocked actuator. In this position, it can be most comfortable for the user to depress the second actuator 306 with his or her thumb. Each of the first and second actuators 304, 306 of the first operator control interface 300 can be operatively and/or electrically connected to the motor 420 of the ball joint mechanism 400 and/or the brake(s) 270 of one or more of the joints 220a, 220b, 220c in a manner requiring BOTH actuators 304, 306 be enabled in order to free the mechanism. Thus, in one embodiment, the surgeon or other healthcare professional can move or reposition the patient only through exerting control of the mechanism by engagement of the first actuator 304, then or subsequently by triggering the mechanism by engagement of the second actuator 306. In one embodiment, the actuators 304, 306 could be engaged simultaneously to produce or permit the desired movement.

The first operator control interface 300 is not limited to inclusion of two separate, spaced-apart actuators. For example, the first operator control interface 300 could include three or more actuators, depending upon the desired functionality of the system. An additional actuator 307 (see FIG. 1) can be located on an opposite end of the body 302 from the second actuator 306. The position or location of the additional actuator 307 can enable a similar actuation as that described above when the first operator control interface 300 is in a configuration upside down to that shown in FIG. 1, which can occur during rotation or flipping of the patient on certain surgical (e.g., spine) tables.

As with all components described herein, the first operator control interface 300 is not limited to the exact size, configuration and/or positioning shown in the figures attached hereto. Although the body 302 is shown as being generally cylindrical and having a longitudinal axis that extends generally in the plane defined by the link arms 218*a*, 218*b*, the presently disclosed technology is not so limited. For example, in an alternative embodiment, the longitudinal axis of the body 302 can extend generally perpendicular to the plane defined by the link arms 218*a*, 218*b*, and can only include the first actuator 304 at one end or side thereof.

The body 312 of the first operator control interface 300 can be spaced-apart from the ball joint 410 and an attachment mechanism 310 of the first operator control interface 300. In particular, the body 312 can be attached to an upper or output side of the ball joint 410 by a shaft 312. Thus, the attachment mechanism 310 can be spaced-apart from the body 302 and be permanently and/or fixedly attached thereto by a shaft 312. Such a configuration allows a user (e.g., surgeon) to move or drive all axes of the system when the brake(s) 270 and the motor 420 are in the released state.

The attachment mechanism 310 can include one or more features that permit permanent or removable attachment to the ball joint mechanism 400, one or more head supports, a second operator control interface 332, and/or a third operator control interface 240 (described in detail below). For example, a rotatable knob 314 or tightening clamp (see FIG. 2) can be configured to move (e.g., open and/or close) vice-like jaws 321*a*, 321*b* that can be configured to grasp a portion of a head support therebetween. In one embodiment, the grasped portion of the head support can snap into place by depression of an interior button 322. If the jaws 321*a*, 321*b* are not sufficiently tightened by the knob 314 to properly clamp a head support, the interior button 322 can function as a safety catch so the head support will not inadvertently separate from the attachment mechanism 310. A release button 316 (see FIG. 1) can allow the head support to be removed or separated from the attachment mechanism 310. Thus, a second action (e.g., depressing the release button 316) can be necessary to remove the head support from the attachment mechanism 310.

The attachment mechanism 310 can further include a first receptacle 318 and a second receptacle 320. A longitudinal axis of the first receptacle 318 can extend perpendicularly to a longitudinal axis of the second receptacle 320. The first receptacle 318 can be sized, shaped and/or configured to receive at least a portion one or more of the head supports (as described in detail below), and the second receptacle 320 can be sized, shaped and/or configured to receive at least a portion of the third operator control interface 240 (as described in detail below). Each of the receptacles 318, 320 can include one or more exposed electrical contacts (e.g., pogo pins). It is understood by those skilled in the art that the receptacles 318, 320 are not limited to be located on or in the attachment mechanism 310. For example, either or both of the receptacles 318, 320 can be formed on or in the ball joint mechanism 400, the body 302 of the first operator control interface 300, the distal end 204 of the arm assembly 200 or the first link arm 218*a*.

As shown in FIGS. 1, 2 and 16-18, the position of the first operator control interface 300 relative to other components of the system can be advantageous. Particularly during initial set-up of the system 100 and/or prior to surgery, it can be beneficial for the first operator control interface 300 to be located proximate to the upper end of the ball joint mechanism 400 and/or the distal end 204 of the arm assembly 200. Such proximity allows the surgeon or other healthcare professional to have his/her hand near the free end of the arm assembly 200 and make minute or finite changes in the position of the free end of the arm assembly 200, thereby facilitating attachment to a variety of attachments, such as a head support (embodiments described in detail below).

Referring to FIGS. 7-10 and 16-18, one or more head supports can be removably attachable or fixable to one or more portions of the support or apparatus, generally designed 100, of the presently disclosed technology. The system or apparatus 100 can include or be attached to a variety of different types of head supports depending upon the medical procedure and/or the patient's condition. One embodiment of a head support is a head clamp 330 shown in FIGS. 7, 17 and 18. The head clamp 330 can be beneficial for long, more intrusive procedures that require more precise head control. Generally, head clamps are known in the art. However, one unique feature of the head clamp 330 of the presently disclosed technology is the manner in which it is removably attachable to a remainder of the system or apparatus.

Figure 8:
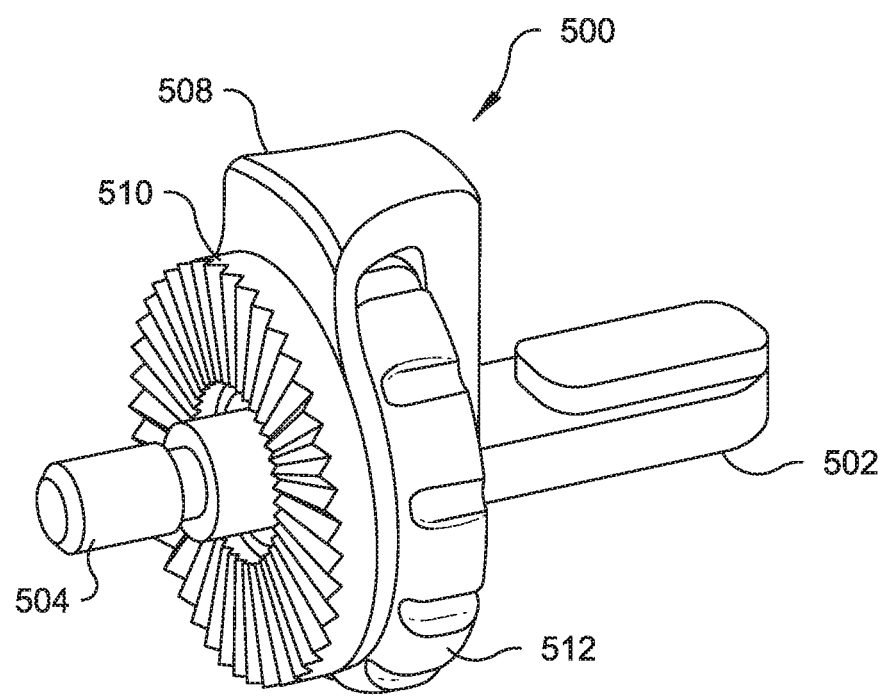
FIG. 8 is a magnified perspective view of a segment of the structure shown in FIG. 7.

In one embodiment, as shown in FIG. 8, an adapter, generally designated 500, can permit the head clamp 330 to be removably attachable to the attachment mechanism 310 of the first operator control interface 300. The adapter 500 can also be used to secure or fix the head clamp to the arm assembly 200 or the remainder of the system 100, such that the operator is able to selectively position and/or orient the patient's head about any axis. A first or distal end 504 of the adapter 500 can be sized, shaped and/or configured to be inserted into at least a portion of the head clamp 330. An opposing second or proximal end 502 (e.g., a second mount) of the adapter 500 can be sized, shaped and/or configured to be inserted into at least a portion of the second receptacle 320 of the attachment mechanism 310. More particularly, in one embodiment, at least a portion of the second end 502 can be inserted into the second receptacle 320 of the attachment mechanism 310. In operation of one embodiment of the presently disclosed technology, the first end 504 can be installed on the head clamp 330 before the head clamp 330 is attached to the patient. Once the head clamp 330 is installed on the patient, the patient can be moved or rolled into position, and then the second end of the adapter 500 can be inserted into the attachment mechanism 310 or otherwise attached to the arm assembly 200.

The adapter 500 can include a wheel 512 that can rotate with respect to a remainder and/or a body 508 of the adapter 500. The wheel 512 can be fixedly attached to the first end 504, which can include one or more threads on an exterior surface thereof. The wheel 512 can be configured to be grasped or touched by the surgeon or other healthcare provider, such that rotation of the second portion 512 can rotate the first end 504, thereby moving the first end 504 into or out of engagement with a mating female thread of the head clamp 330. Thus, the wheel 512 can be rotated to tighten the adapter 500 to the head clamp 330. As a result, the second end 502 of the adapter 500 can serve as a quick connection into the attachment mechanism 310 (e.g., the second end 502 can latch into position (via the interior button 322), and then the second end 502 can be clamped tightly into the attachment mechanism 310). This quick connection can be beneficial as it can limit the time the surgeon or other healthcare professional needs to steady the patient's head while engaging the head clamp 330 to the first operator control interface 300.

A plate 510 or a portion of the body 508 can include a series of spaced-apart ridges or teeth 514 that can be sized, shaped and/or configured to complementarily engage spaced-apart grooves or teeth of the head clamp 330. The combination of complementary teeth can lock or fix the head clamp 330 to the adapter 500, which in turn can be locked to the attachment mechanism 310. In one embodiment, the plate 510 can be removably attachable to the body 508. In one embodiment, the system 100 can include two or more plates 510, each of which can have a unique teeth pattern or size. The plates 510 can be selectively attached to or removed from the body 510 to accommodate different brands or styles, for example of head clamps 330.

Figure 9:
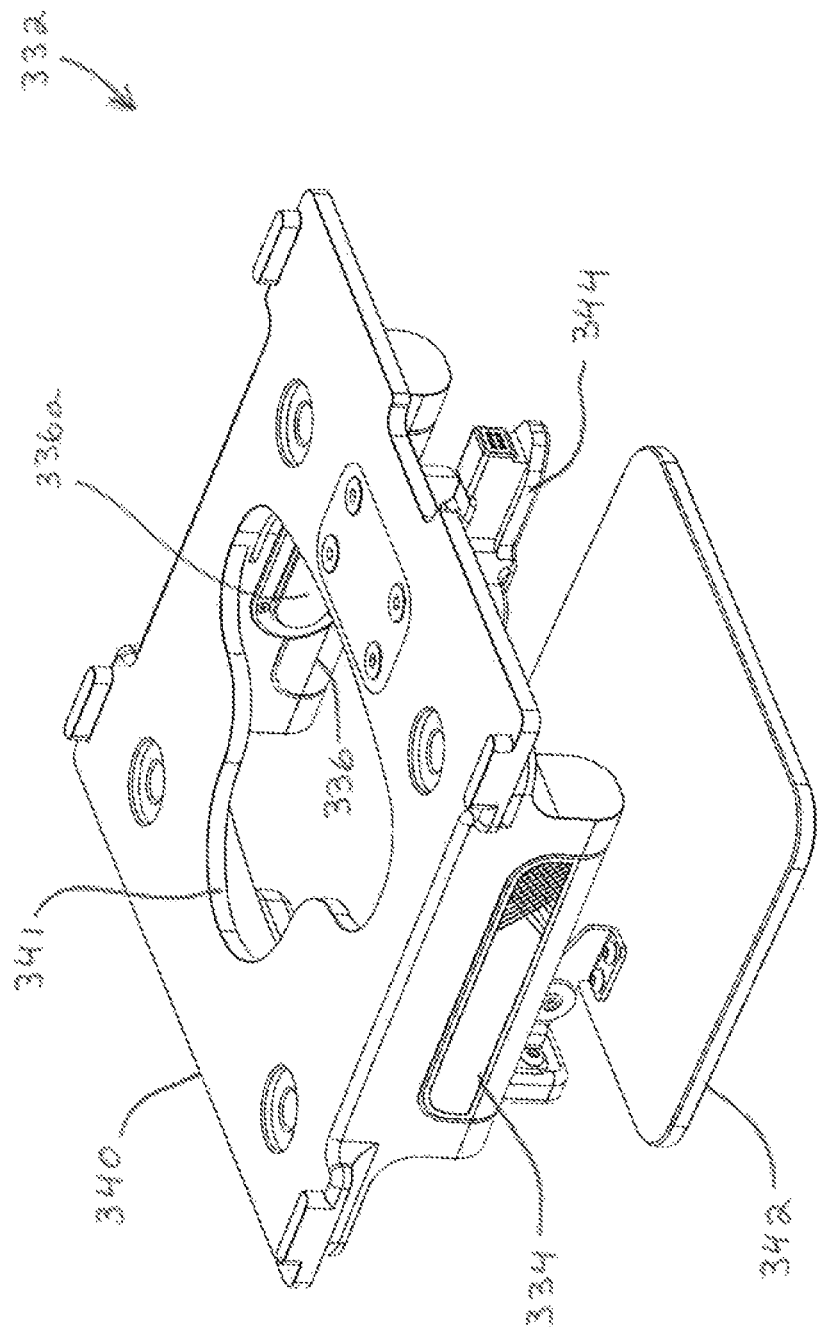
FIG. 9 is a perspective view of an embodiment of still another component of the system or apparatus according to an embodiment of the present disclosure.
Figure 10:
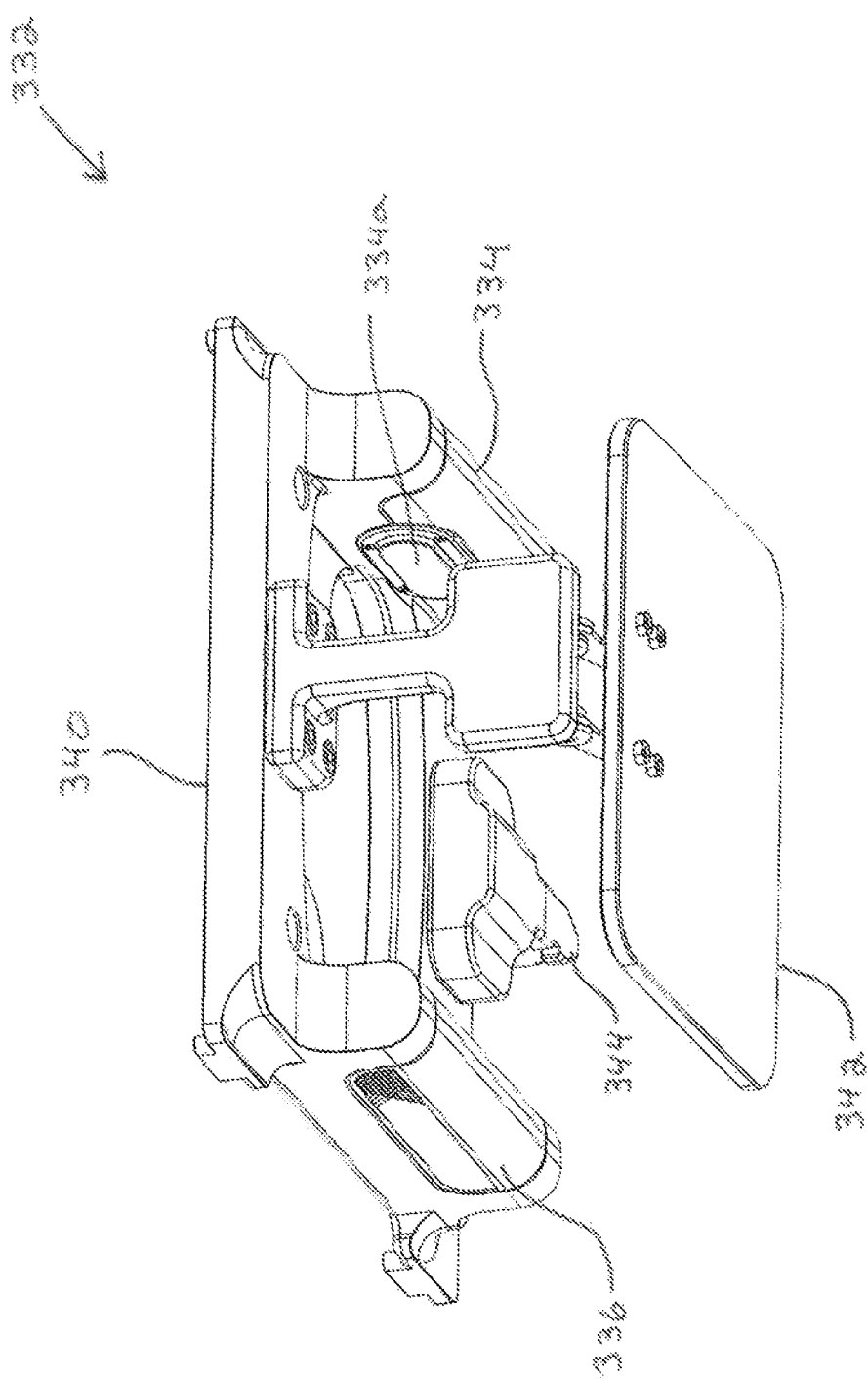
FIG. 10 is another perspective view of the component shown in FIG. 9.
Figure 16:
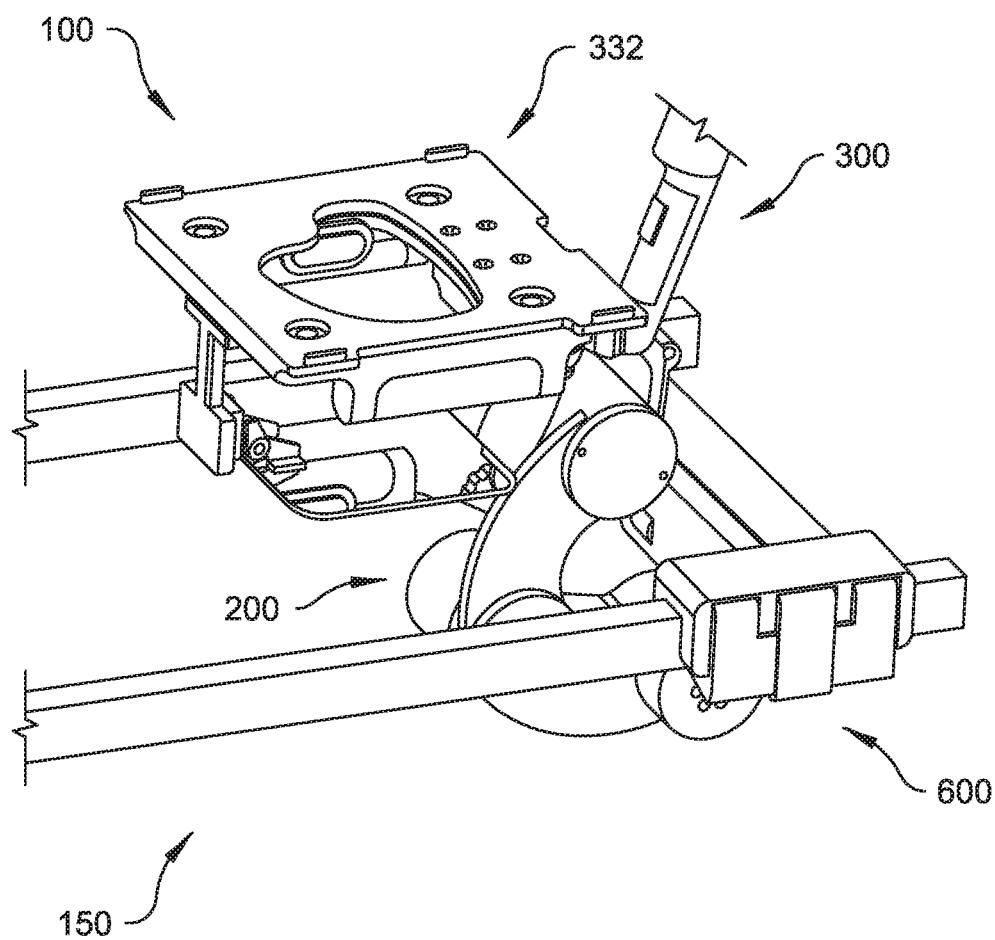
FIG. 16 is a perspective view of one configuration of at least certain components of the present disclosure.

Another embodiment of a head support is a head support plate 332 shown in FIGS. 9, 10 and 16. A conventional support mask, helmet, pillow or other device can be mounted onto the head support plate 332. The head support plate 332 can be beneficial for shorter, less intrusive or invasive procedures that require less head control, or for lumbar or thoracic spine procedures where the cervical spine is not compromised. The head support plate 332 can include an upper plate 340 spaced-apart from a lower plate 342. The upper plate 340 can include an opening 341 therein, and the lower plate 342 can include a mirrored surface or portion. At least a portion of the patient's face can be placed in or aligned with the opening 341. The lower plate 342 can move or pivot with respect to the upper plate 340. This configuration allows a healthcare professional, such as an anesthesiologist, to easily and quickly see the patient's face during the medical procedure. A projection 344 (e.g., a third mount) with one or more exposed electrical contacts can extend outwardly from the head support plate 332. At least a portion of the projection 344 can be sized, shaped, and/or configured to matingly engage one or both the first and second receptacles 318, 320 of the attachment mechanism 310 of the first operator control interface 300, such that the electrical contact(s) of the projection 344 can engage the electrical contact(s) of the first receptacle 318 or the second receptacle 320.

The head support plate 332 can include or be in the form of the second operator control interface. More particularly, the head support plate 332 can include a first or left handle 334 spaced-apart from a second or right handle 336. In one embodiment, each of the first and second handles 336 can be positioned on a bottom side of the upper plate 340, and can be engaged when moved or pressed upwardly toward a top surface of the upper plate 340. Each of the first and second handles 334, 336 of the head support plate 332 can be operatively and/or electrically connected to the motor 420 of the ball joint mechanism 400 and/or brake(s) 270 of one or more of the joints 220a, 220b, 220c. In one embodiment, each handle 334, 336 can include an actuator or release trigger 334a, 336a on an inside surface thereof. Such a design can require the user to wrap his or her fingers completely around each handle 334, 336 before the actuator 334a, 336a can be exercised, engaged or depressed. In this embodiment, each of the first and second handles 334, 336 and the actuators 334a, 336a of the head plate 332 can be operatively and/or electrically connected to the motor 420 of the ball joint mechanism 400 and/or brake(s) 270 of one or more of the joints 220a, 220b, 220c. One goal of such an embodiment can be to require the user to exert control over the system 100 and/or head support plate 332 before the brake(s) 270 and ball joint 410 can be released. In one embodiment, it can be required that both the left and right triggers 334a, 336a be actuated before the brake(s) 270 is/are released, thus ensuring the safety of the system 100 and the head support plate 332. In on embodiment, the head plate 332 can include a rotatable knob similar in structure and functionality to that described below for the third operator control interface.

Thus, with the patient's head supported on or by the head support plate 332, the surgeon or other healthcare professional can selectively move the head support plate 332 and/or the patient's head by engagement of one or both of the first and second handles 334, 336 and/or the actuators 334a, 336a. The positioning of the first and second handles 334, 336 and/or the actuators 334a, 336a can be advantageous, as the surgeon or other healthcare professional can have his/her hands very close to the patient's head during movement of the head support plate 332. This gives the surgeon or other healthcare professional increased control of the movement of the patient. In addition, the surgeon or other healthcare professional would not be required to go behind or beneath the surgical drape to move or reposition the patient.

Figure 11:
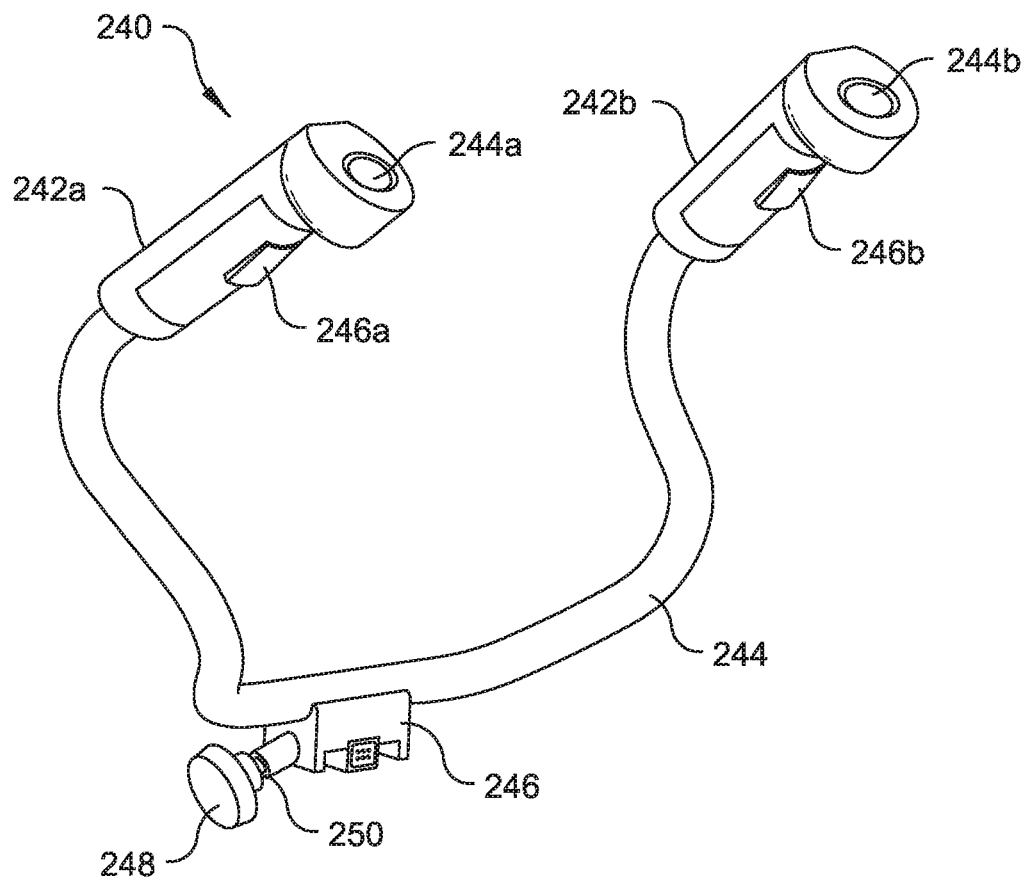
FIG. 11 is a perspective view of an embodiment of a component of the system or apparatus according to an embodiment of the present disclosure.

FIG. 11 shows a perspective view of a third operator control interface 240. The third operator control interface 240 can include one or more spaced-apart handles 242a, 242b, which can be coupled to extensions or "horns" 244 that are attached to a housing 246 (e.g., fourth mount). The housing 246 can include one or more exposed electrical contacts. At least a portion of the housing 246 can be sized, shaped and/or configured to engage or be received in one or both of the first and second receptacles 318, 320 of the attachment mechanism 310 of the first operator control interface 300, such that the electrical contact(s) of the housing 246 can engage the electrical contact(s) of the first receptacle 318 or the second receptacle 320. A rotatable knob 248 can be fixed to a shaft 250 that is insertable into and extendable through at least a passageway in the housing 246. The knob 248 can allow the surgeon or other healthcare professional to tighten, lock or more securely attach the third operator control interface 240 to the first operator control interface 300, and/or loosen or prepare to release the third operator control interface 240 from the first operator control interface 300.

Each handle 242a, 242b can include one or more an actuators 244a, 246a, 244b, 246b. Two or more of the actuators 246a, 246b can be in the form of a spring-actuated trigger or tab, which can be depressed and/or engaged by a user's palm when the user grasps the handle 242a, 242b, respectively. Two or more of the actuators 244a, 244b can be in the form a spring-actuated push button, which can be depressed and/or engaged by a user's finger. In operation, when the user grasps the handle 242a, 242b, it can be most comfortable for the user to depress the actuators 244a, 244b with his or her thumb. Each of the actuators 244a, 246a, 244b, 246b of the third operator control interface 240 can be operatively and/or electrically connected to the motor 420 of the ball joint mechanism 400 and/or brake(s) 270 of one or more of the joints 220a, 220b, 220c. It is understood that the actuators 244a, 244b, 246a, 246b can be coupled to the joints 220a, 220b, 220c and/or the ball joint mechanism 400 in any appropriate manner. As a result of the coupling or connection, the surgeon or other healthcare professional can move or reposition the patient through engagement of one or both of the actuators 244a, 246a, 244b, 246b.

In operation of one embodiment, the handles 242a, 242b allow accurate positioning of the patient's head, through movement of the head clamp 230, for example, when the joints 220a, 220b, 220c and/or the ball joint mechanism 400 are in an unlocked state. This can be accomplished by the surgeon, or other personnel, grasping one or both of the handles 242a, 242b and actuating the actuators 244a, 244b after actuating the actuators 246a, 246b, to place the joints 220a, 220b, 220c and/or the ball joint mechanism 400 in an unlocked state and moving the handles 242a, 242b to desired positions. Releasing the actuators 244a, 244b, 246a, 246b can place the joints 220a, 220b, 220c and/or the ball joint mechanism 400 in a locked state to retain the desired position. This configuration does not permit inadvertent movement of the patient's head or when the surgeon does not have a balanced, two-handed, grasp of the handles 242a, 242b.

In one embodiment, the surgeon can be required to engage (e.g., firmly grip) both handles 242a, 242b before he/she is able to release the brake(s) 270 and/or the joint(s) 220. In this embodiment, an algorithm of the system 100 can require that both enable buttons 246a, 246b be engaged, depressed or fully depressed before any motion of the system 100 is permitted or possible. Then, with a firm grip established, the surgeon can easily and ergonomically release one or both trigger buttons 244a, 244b. This will provide a high level of safety by assuring the physician is ready and capable to support the weight of the patient's head.

Furthermore, the algorithm can allow for three modes of release. For example, in one embodiment, if only one trigger button 244a, 244b is actuated or depressed, the ball joint 410 can unlock allowing coronal plane and roll motion. If the other trigger button 244a, 244b is actuated or depressed, one or more of the brakes(s) 270 can be released, thereby allowing sagittal plane adjustment. If both trigger buttons 244a, 244b are released or engaged together or simultaneously, then all joints (e.g., each brake 270 and the ball joint 410) can be released. As soon as any enable or trigger button 244a, 244b is released, all axes can immediately lock-up.

Referring to FIGS. 12-18, the system or apparatus can include a base to removably attach the arm assembly 200 to the support apparatus 150. It can be beneficial if the arm assembly 200 is able to move with respect to the support apparatus 150 to provide the surgeon or other healthcare professional with additional options for moving or repositioning the patient. Thus, it can be beneficial that the base of the presently disclosed technology can move in two degrees (e.g., in an X direction and in a Y direction) with respect to the support apparatus 150.

Figure 12A:
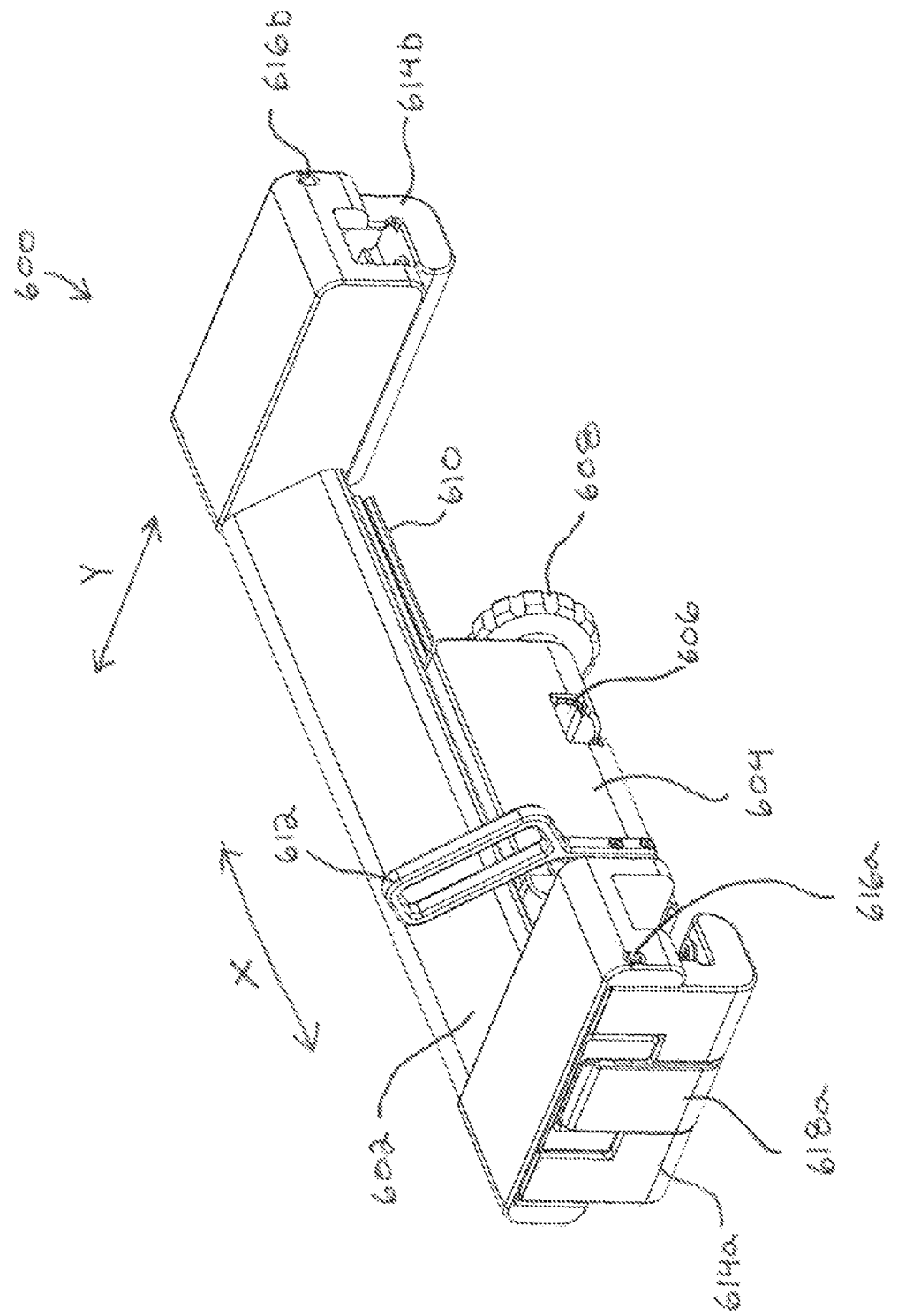
FIG. 12 is a perspective view of an embodiment of a further component of the system or apparatus according to an embodiment of the present disclosure.

As shown in FIGS. 12, 13 and 16, one embodiment of the base, generally designated 600, can include a first body 602 and a second body 604. The first body 602 can be configured to contact or attach directly to a portion of the support apparatus 150. The second body 604 can include a receptacle 606 that can be sized, shaped and/or configured to receive at least a portion of the body 260 of the first mount 230. A rotatable knob 608 can be fixed to a shaft that is insertable into and extendable through at least a passageway in the second body 604. The knob 608 can allow the surgeon or other healthcare professional to tighten or more securely attach the arm assembly 200 to the base 600, and/or loosen or prepare to release the arm assembly 200 from the base 600.

The second body 604 can be configured to move with respect to the first body 602. More particularly, a portion of the second body 604 can include one or more ball or roller bearings that can engage and/or ride on a rail 610 of the first body 602. Thus, the second body 604 can move generally perpendicularly to a longitudinal axis of the patient and/or a plane in which the arm assembly 200 extends. A locking tab or handle 612 can be attached to the second body 604, and can be movable between a first or locked position and a second or unlocked position. In the locked position, the locking tab 612 can engage a brake mechanism that grasps at least a portion of the first body 602 (e.g., the rail 610) or otherwise prevents the second body 604 from moving with respect to the first body 602. In the unlocked position, the brake mechanism is released and/or the locking tab 612 does not interfere with or can permit the second body 604 to be moved with respect to the first body 602. In one embodiment, to move the second body 604 with respect to the first body 602, the locking tab 612 can be rotated from the locked position to the unlocked position. The surgeon or other healthcare professional can grasp or otherwise touch a portion of the system 100, such as the arm assembly 200, the skull clamp 330, the steer horns 240 or the prone platform 332 and easily move or adjust the second body 604 laterally. This allows the surgeon place the patient's head exactly where he/she needs it. The rail 610 and bearing(s) provide the low friction and rigidity to make this nearly effortless.

The first body 602 can be configured to lock onto and/or move or slide with respect to the support apparatus 150. In particular, in one embodiment, opposing lateral sides of the first body 602 can each include a two-part or two-stage clasp mechanism. For the sake of brevity and convenience only, portions of the below description may focus on the clasp mechanism on only one of the lateral sides of the first body 602, though it is understood that the opposing lateral side can include the mirror structure and functionality. More particularly, one or each opposing side of the first body 602 can include a first clasp 614a, 614b that can include and be fixed to a pin 616 that extends along a Y axis (e.g., parallel to the direction in which the patient extends). As shown in FIGS. 13B-F, the pin 616 can engage and/or extend through a slot in a housing 628 of the first body 602, which can enable the pin 616 (and thus the first clasp 614) to pivot (e.g., rotate) and/or translate (e.g., move linearly) vertically.

Figure 13B:
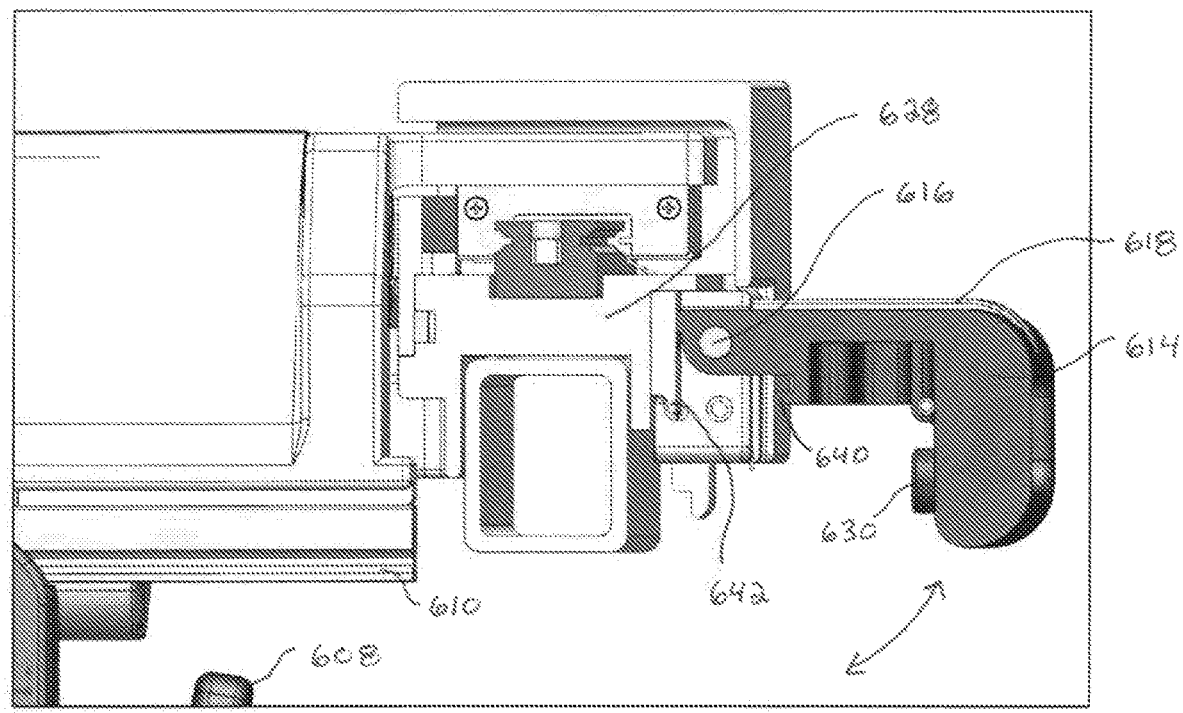
FIG. 13B is a cross-sectional side elevational view of a portion of the component shown in FIG. 13A, wherein two clasps are shown in a fully open or upward position and wherein the cross-section is taken through the first or larger clasp.
Figure 13C:
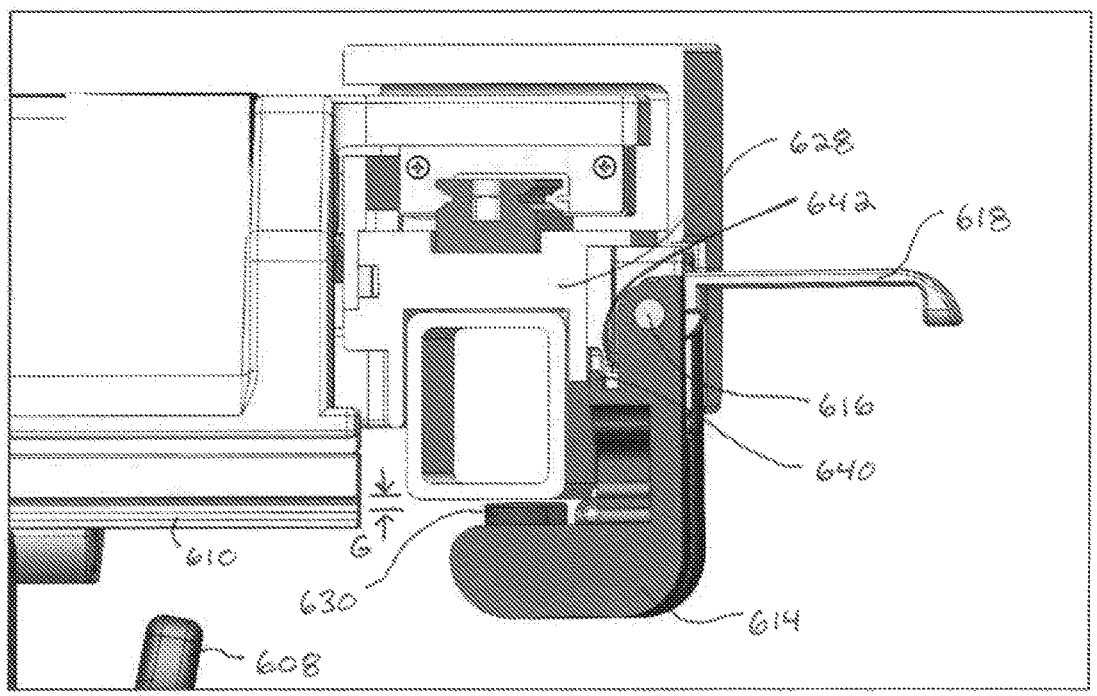
FIG. 13C is another cross-sectional side elevational view of a portion of the component shown in FIG. 13A taken along the same plane as in FIG. 13B, wherein one clasp is shown in a closed position and another clasp is shown in a fully open or upward position.
Figure 13D:
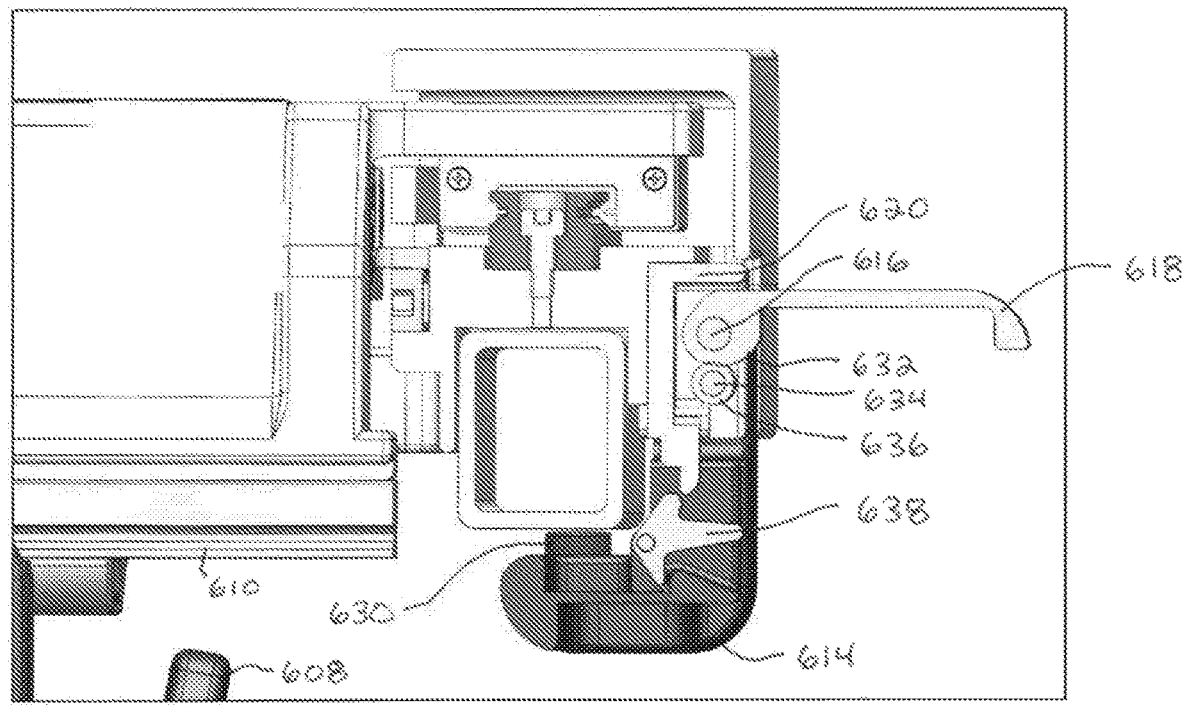
FIG. 13D is a cross-sectional side elevational view of a portion of the component shown in FIG. 13A taken along a different plane than FIGS. 13B and 13C, wherein the clasps are shown in the same orientation as shown in FIG. 13C and wherein the cross-section is taken through the second or smaller clasp.
Figure 13E:
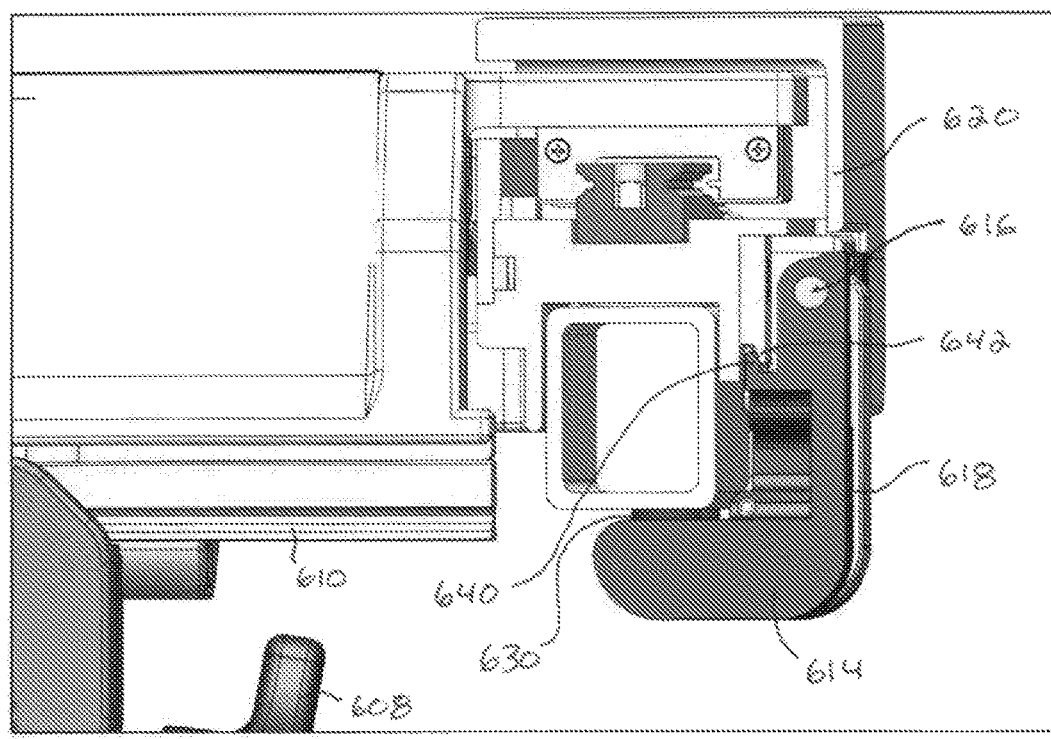
FIG. 13E is yet another cross-sectional side elevational view of a portion of the component shown in FIG. 13A taken along the same plane as FIGS. 13B and 13C, wherein both clasps are shown in a closed position.
Figure 13F:
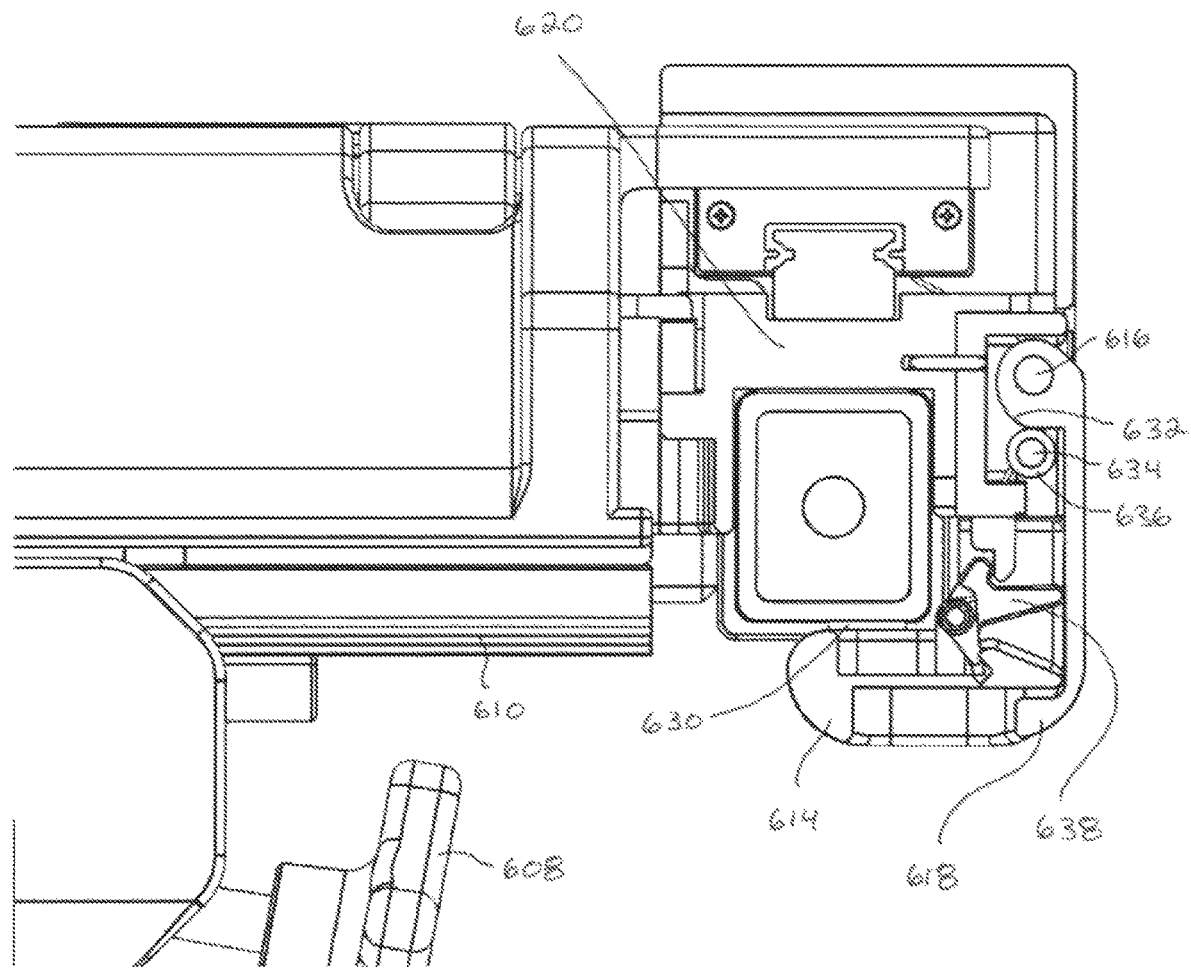
FIG. 13F is a magnified cross-sectional side elevational view of a portion of the component shown in FIG. 13A taken along the same plane as FIG. 13D, wherein both clasps are shown in a closed position.
Figure 15:
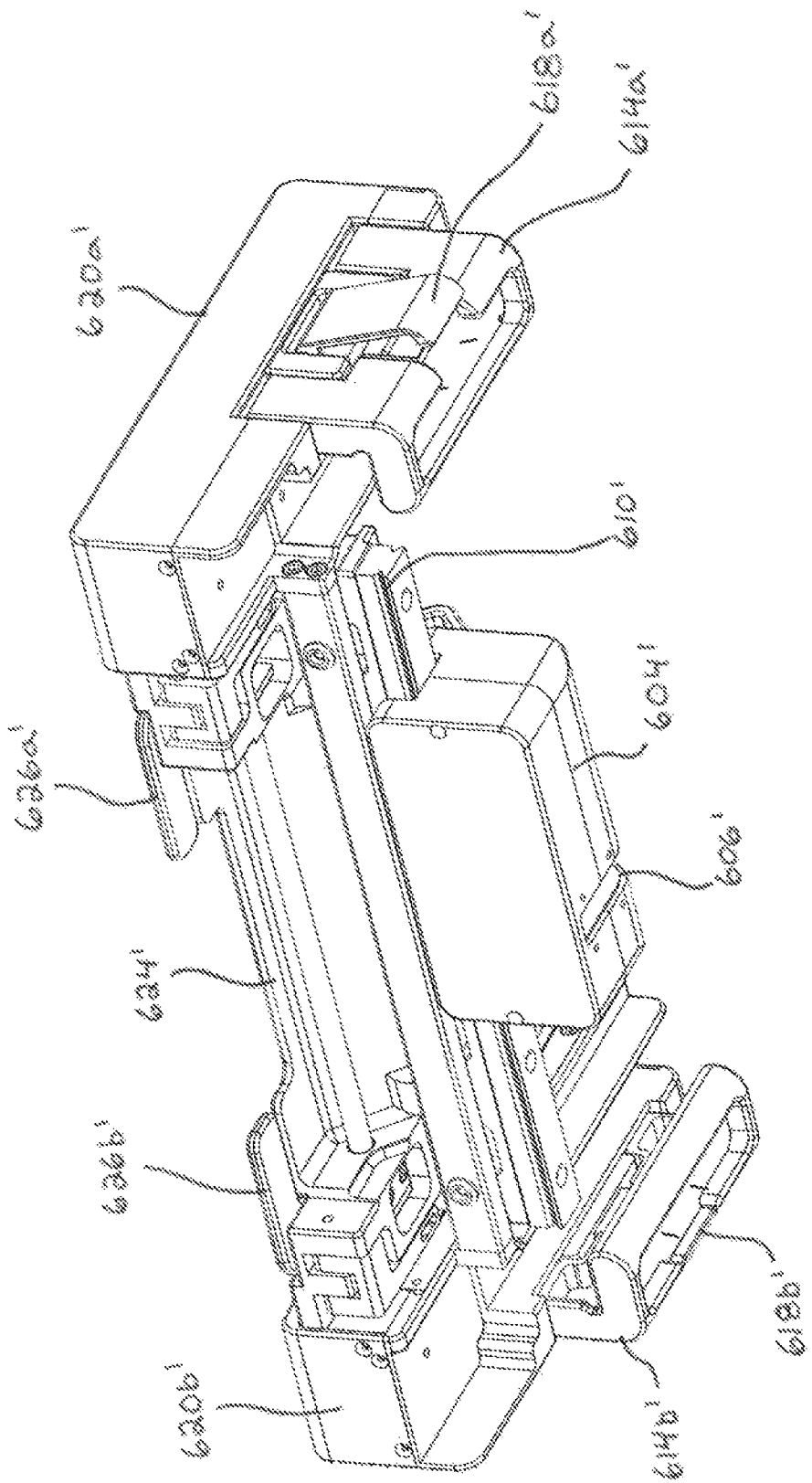
FIG. 15 is another perspective view of the component shown in FIG. 14.

Each first clasp 614a, 614b can include a portion that extends vertically downwardly from the pin 616a, 616b and another portion that extends generally perpendicularly thereto to extend beneath at least a portion of the support apparatus 150. The segment of the first clasp 614 that can be positionable below the support apparatus 150 (e.g., the "horizontal" segment of the first clasp 614) can include one or more spaced-apart compressible friction members 630. In one embodiment, each compressible friction member 630 can be a rubber grommet. Each first clasp 614a, 614b can move between a first, non-engaged position and a second, engaged position (see FIGS. 12 and 13A-F). One or each opposing side of the first body 602 can also include second clasps 618a, 618b that can pivot about the pin 616 and can be positioned in a longitudinal midsection of the first clasp 614a, 614b. Each second clasp 618a, 618b can move, rotate and/or pivot with respect to the respective first clasp 614a, 614b. Similar to the first clasps 614a, 614b, each second clasp 618a, 618b can move between a first, non-engaged position (see, e.g., FIGS. 13B-13D) and a second, engaged position (see FIGS. 12, 13A, 13E and 13F). As shown in FIGS. 13D and 13F, each second clasp 618 can include a cam or cam surface 632, which can selectively engage a second pin 634 fixed in the housing 620 and/or a roller 636 that can surround the second pin 634.

In one embodiment, when the second clasp 618 is in the second, engaged position, the cam surface 632 of the second clasp 618 can act against the second or fixed pin 634 and roller 636 (see FIG. 13F), thereby causing the first clasp 614 to move upwards, forcing the compressible friction member(s) 630 into engagement with at least a portion of the support apparatus 150, such that the base 600 cannot move with respect to the support apparatus 150 along the Y or longitudinal axis. In operation, the compressible friction member(s) 630 can be at least slightly compressed under the force of engagement with the first clasp 614 and the support apparatus 150, thereby creating a high friction surface. When the second clasps 618a, 618b are in the first, non-engaged position (see FIGS. 13B-13D), the first clasps 614a, 614*b* can either be (i) in the first, non-engaged position such that the base 600 can be separated from the support apparatus 150 (see FIG. 13B) or (ii) in the second, engaged position such that the base 600 can contact and/or move with respect to the support apparatus 150 along the Y or longitudinal axis (see FIGS. 13C and 13D). At least a slight clearance gap G (see FIG. 13C) between the housing 628 or another portion of the first body 602 and the grommet(s) 630, when the first clasp 614 is in the downward position but the second clasp 618 is in the upward position, can enable or allow for the movement of the base 600 with respect to the support apparatus 150. Thus, the first clasps 614*a*, 614*b* can function to (i) generally hold the base 600 in place on the support apparatus 150, (ii) generally prevent inadvertent movement thereof, and/or (iii) allow the base 600 to slide or otherwise move with respect to the support apparatus 150 without being separated from the support apparatus. The second clasps 618*a*, 618*b* can function to generally lock the base 600 in place on the support apparatus 150.

In one embodiment, the first clasps 614*a*, 614*b* are configured to rotate into position under the table support spars and latch into position. A spring-actuated finger latch 638 can be positioned in a longitudinal midsection of each first clasp 614. The latch 638 can be covered or otherwise at least partially concealed by the second clasp 618 when the second clasp 618 is closed or rotated downwardly (see FIGS. 13C-13F), but at least partially exposed or visible to the user when second latch 618 is open or rotated upwardly (see FIGS. 13A and 13D). The latch 638 can be configured to hold the first clasp 614 in the latched, locked or downward orientation by engaging a portion of the housing 628 or other portion of the first body 602. In one embodiment, as shown in FIG. 13D, the user or surgeon can be required to engage and/or rotate the latch 638 (e.g., clockwise in FIG. 13D) to allow the first clasp 614 to reopen. The cam or cam surface 632 of the second clasp 618 can drive the first clasp 614 upwardly and thereby enable it to grip at least a portion of one of the spars of the support apparatus 150. As shown in FIGS. 13C and 13E, passive or complementary locking tabs 640, 642 on the first clasp 614 and the housing 628, respectively, can engage in this position, assuring the that first clasp 614 cannot be opened by any jarring impact. This combination allows for three independent or separate states of the clasp mechanism: (i) both fully open and unlocked so that the base 600 can be placed on the table 150, (ii) first clasps 614*a*, 614*b* latched so the base 600 cannot be lifted off the table 150, yet it is free to translate along the table 150, (iii) the second clasps 618*a*, 618*b* latched, which drives the first clasps 614*a*, 614*b* upwardly to grip the table 150 tightly so the base 600 is fully constrained.

As shown in FIGS. 14, 15, 17 and 18, a second embodiment of the base, generally designated 600', can include many or all of the features of the base 600 of the first embodiment. The same or similar features of the base 600' of the second embodiment are shown with the same reference number as in the first embodiment, but with the addition of a prime (') symbol. A description of the same or similar features is omitted herein for the sake of clarity and brevity only. One distinguishing feature of the base 600' of the second embodiment is that the first body 602' can include three or more components that are configured to move relative to one another, thereby adding an additional degree of control or movement to the system.

In particular, the first body 602' can include a first end 620*a*', a second end 620*b*', and a mount 624' therebetween. The mount 624' can move (e.g., slide) with respect to the first and second ends 620*a*', 620*b*'. More particularly, opposing ends of the mount 624', which contact or engage the first and second ends 620*a*, 620*b*', respectively, can include one or more ball or roller bearings that can engage and/or ride on at least a portion of the first and second ends 620*a*', 620*b*'. Thus, in addition to the horizontal or lateral movement that the second body 604' can provide, the first body 602' of the second embodiment of the base 600' can provide longitudinal movement. As shown in FIG. 14, a top surface of each of the first and second ends 620*a*', 620*b*' can include distance markings or a ruler, which can be used to track the relative movement of the mount 624' to the first and second ends 620*a*', 620*b*' to help the surgeon or other healthcare professional position or reposition the patient.

At least one or two or more locking levers or handles 626*a*', 626*b*' can be attached to the mount 624', and can be movable (e.g., rotatable) between a first or locked position and a second or unlocked position. In the locked position, each locking lever 626*a*', 626*b*' can grasp at least a portion of the first and second ends 620*a*', 620*b*', respectively, or otherwise prevent the mount 624' from moving with respect to the first and second ends 620*a*', 620*b*'. In the unlocked position, each locking lever 626*a*', 626*b*' does not interfere with or can permit the mount 624 each locking lever 626*a*', 626*b*' to be moved with respect to the first and second ends 620*a*', 620*b*'. The above-described longitudinal adjustment provided by the base 600' has many benefits. For example, this design can provide easy adjustments during patient set-up to connect the arm assembly 200 to the skull clamp 330 rather than releasing the second clasps 618*a*', 618*b*' and sliding the entire unit. This design can provide increased range of motion during intraoperative adjustments; the low friction allows user to guide the patients head rather than having to push or move the base 600' and/or the first body 602'. This design can provide static traction; the surgeon can release the levers 626*a*', 626*b*', pull the unit and/or the second body 604' longitudinally and apply a certain amount of traction to distend the neck of the patient. This design can provide active traction; the surgeon can release levers 626*a*', 626*b*' and apply a weight bag via pulleys (for example) to the base 600' and/or the second body 604' and apply a constant force traction.

Figure 17:
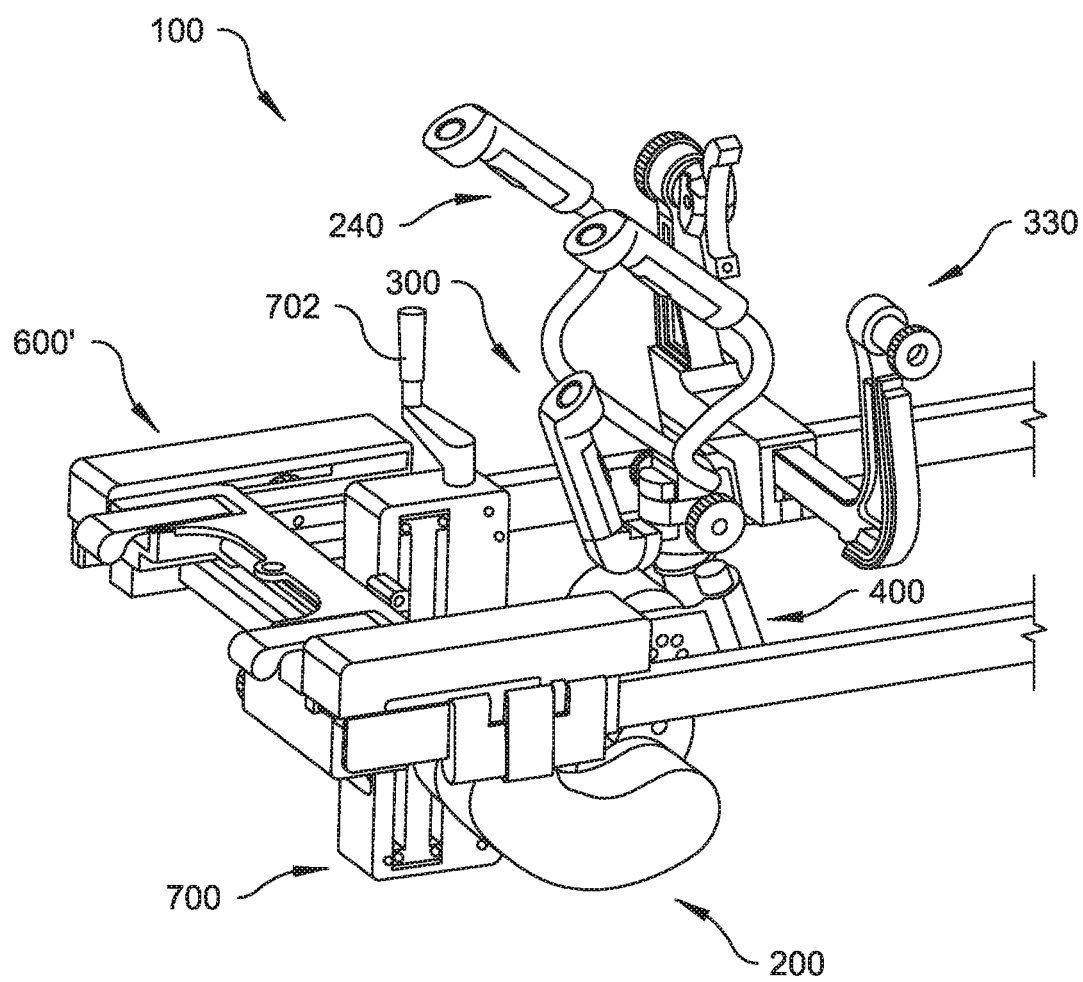
FIG. 17 is a perspective view of a second configuration of at least certain components of the present disclosure.
Figure 18:
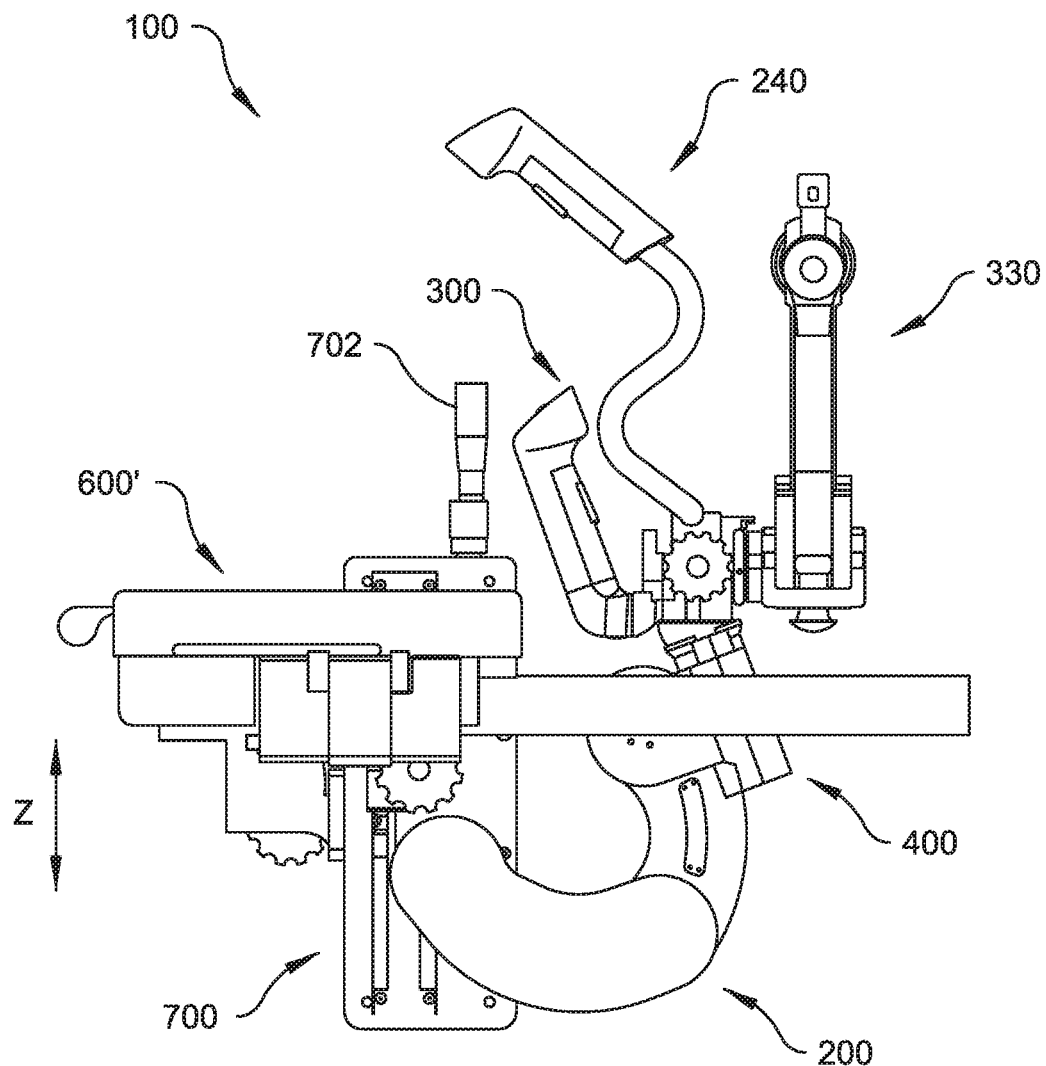
FIG. 18 is a side elevation view of the configuration shown in FIG. 17.

Referring to FIGS. 17 and 18, in one embodiment, instead of the arm assembly 200 being directly attached to the base 600, 600', a tower 700 can be positioned between the arm assembly 200 and the base 600, 600'. More particularly, the first mount 230 of the arm assembly 200 can be inserted into a receptacle of the tower 700, and a projection (e.g., fifth mount) of the tower 700 can be inserted at least partially or completely into the receptacle 606, 606' of the base 600, 600'. The tower 700 can permit the proximal end 202 of the arm assembly 200 to be vertically raised or lowered (e.g., along the Z axis) with respect to the base 600, 600'. A rotatable crank 702 can be located at a top or bottom of the tower 700, which can allow the surgeon or other healthcare professional to selectively raise or lower the proximal end 202 of the arm assembly through any of a variety of different mechanisms (e.g., lead screw or rack and pinion system). The tower 700 can provide move vertical movement or range to the system 100. For example, the tower 700 can provide a "stroke" of six to seven inches.

The term "surgical table" is broadly defined herein to include any structure to which the system 100 can be attached to and supported by during a medical procedure. Any type, style, size and/or configuration of surgical table can be used as part of or attached to the system 100 of the presently disclosed technology. For example, surgical tables disclosed in U.S. Published Application No. 2016/0228315 can be used in combination with the presently disclosed technology. The system 100 is not limited to be used with a surgical table in the form of an H-frame with rectangular supports. Further, various patient support attachments and other devices can be used in combination with the invention.

In operation, at least a portion of one, two or each of the first operator control interface 300, the second operator control interface 332, and the third operator control interface 240 can be engaged or manipulated by the surgeon or other healthcare professional to provide or create the desired inter-operative movement of the patient. In one embodiment, one or more of the actuators or buttons of one or more of the first operator control interface 300, the second operator control interface 332, and the third operator control interface 240 can be engaged to progressively or sequentially release, unlock or lock the ball joint 410 and/or the joints 220a, 220b, 220c. In such an embodiment, one goal can be to sequentially release the brake(s) 270, thereby providing (i) additional movement of the system 100 upon release of each brake 270 and giving the surgeon more control, and/or (ii) slow or predictable transfer of weight from the system 100 to the surgeon and/or other healthcare professional. To perform a different operation in the same embodiment, or in a different embodiment, one or more of the actuators or buttons of one or more of the first operator control interface 300, the second operator control interface 332, and the third operator control interface 240 can be engaged to release, unlock or lock in parallel or simultaneously. Of course, the actuators or buttons could be engaged in any combination of in parallel or in series. For example, in one embodiment, movement (of at least one of the ball joint 410 and/or the joints 220a, 220c, 220c) may not begin until two actuators (e.g., the first actuator 304 and the second actuator 306 of the first operator control interface 300) are depressed or engaged (e.g., either in series or in parallel). In another embodiment, engagement of one of the actuators can allow the system 100 to move in one plane (e.g., the sagittal plane); engagement of a second one of the actuators can release the ball joint 410, thereby allowing for both roll and yawl movement; engagement of both actuators can permit all degrees of motion or movement. In one embodiment, upon engagement of one or each of the actuators or buttons, the system 100 can configured to perform (e.g., begin) the desired movement or motion within approximately 300 milliseconds, which is a typical human reaction time. This is a significant improvement over the prior art, and ensures that patient positioning and repositioning can be done quickly and with relative each by the medical staff.

As shown in FIGS. 16-18, the location and/or position of each of the first operator control interface 300, the second operator control interface 332, and the third operator control interface 240 can be beneficial. In one embodiment, the position of each of the operator control interfaces 300, 332, 240 can allow the surgeon or other healthcare professional (i) to move and/or control the patient's head through the drapes (ii) while scrubbed in, and (iii) while maintaining sight of the surgical site and without relying on assistance from any other person. Each of the operator control interfaces 300, 332, 240 can be accessible from above the patient and/or are exposed above the patient.

Figure 19:
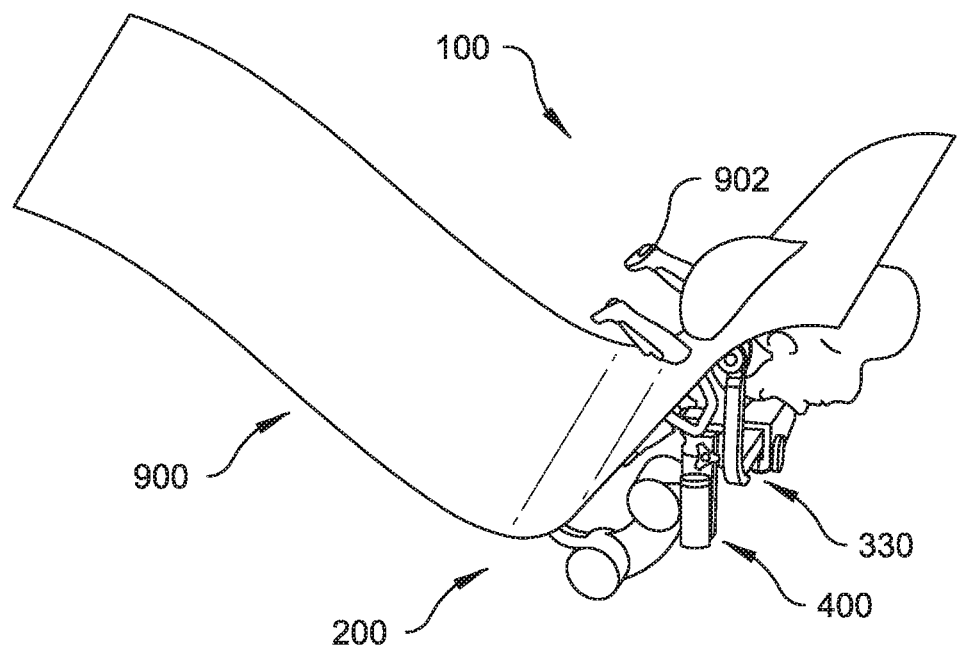
FIG. 19 is a perspective view of one embodiment of a surgical drape used with the system or apparatus.
Figure 20:
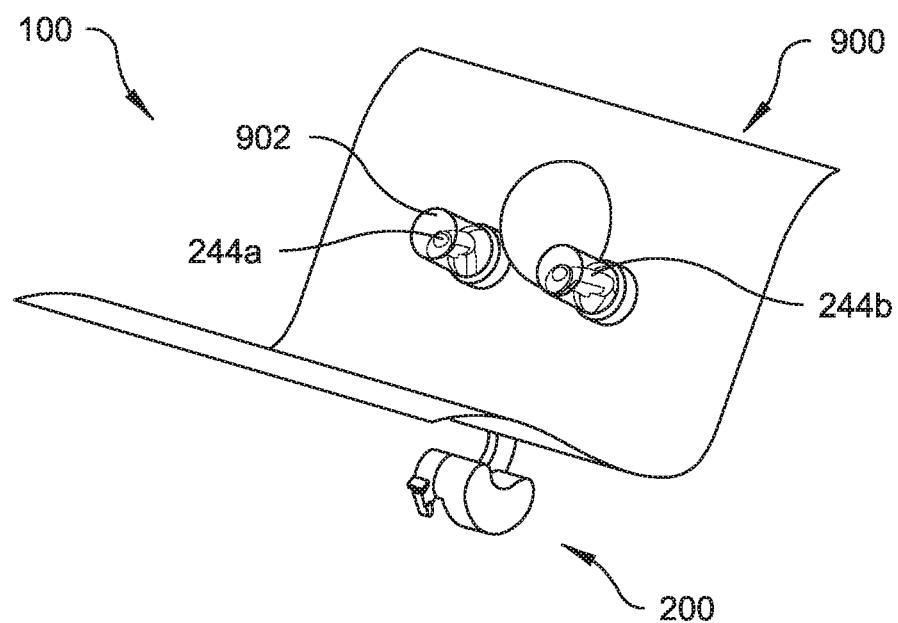
FIG. 20 is another perspective view of the surgical drape used with the system or apparatus.

In one embodiment, as shown in FIGS. 19 and 20, the system 100 is configured to complement and/or can include a surgical drape 900. The drape 900 can be designed to cover at least a portion of, the entirety of, and/or interface with not only to the patient, but also to at least some or all of the operator control interfaces 300, 332, 240 of the system 100. In one embodiment, the drape 900 can allow a sterile surgeon or other healthcare professional (i) to directly move, adjust and/or control the position of the third operator control interface 240 and thus adjust the position and orientation of the patient's head through the drapes (ii) while scrubbed in (i.e., while remaining completely sterile), and/or (iii) while maintaining sight of the surgical site, without disturbing the drape/patient interface at the surgical site, and without relying on assistance from any other person.

Such inter-operative adjustment cannot be done with any prior art system. In contrast, when attempting to move a patient's head in a sterile manner during surgery in prior art systems, one member of the medical team is required to go beneath the surgical table and/or the patient's head, and then rescrub after the adjustment is made. The surgical site remains sterile during this adjustment in prior art systems, but the procedure is can be clumsy, challenging, and time-consuming.

In one embodiment, during a medical procedure, the third operator control interface 240 including the actuators 244a, 244, 246a, 246b can be accessible from above the patient and/or are exposed above the patient and accessible through the drape 900. The drape 900 can be entirely transparent. Alternatively, the surgical drape can be primarily opaque and include one or more spaced-apart transparent windows or pockets 902 to allow the third operator control interface 240 to be identified, grasped and/or engaged through the draft 900 by the user or surgeon. Thus, the drape 900 can be contoured to allow the third operator control interface 240 to be identified and easily gripped through the drape 900 by the user, without disturbing the drape 900 at the location of the surgical site. A transparent sock can be applied to at least a portion of the third operator control interface 240 prior to the application of the drape 900 to provide a second transparent protective barrier. Other embodiments of the drape 900 can provide interfaces or pockets to the first and second operator control interfaces 300, 322 and/or other actuators or controls 612, 626a', 626b' of the system 100 in similar manners.

The electrical nature of the system 100 can also provide feedback when movement of any portion of the system 100 occurs. For example, upon engagement of one of the actuators and movement of at least one of the joints 220, 220b, 220c, the system 100 can emit a tone, display an image or word on a monitor, illuminate a light or series of lights, or the like. The feedback can also be in the form of data, such as the speed, angle, range, displacement, etc. of the movement. Such feedback can be helpful to a surgeon or other healthcare professional in any of a variety of ways, such as for teaching others how to perform surgery, for repeating successful surgeries, and/or for legal matters, such as malpractice claims.

Figure 21:
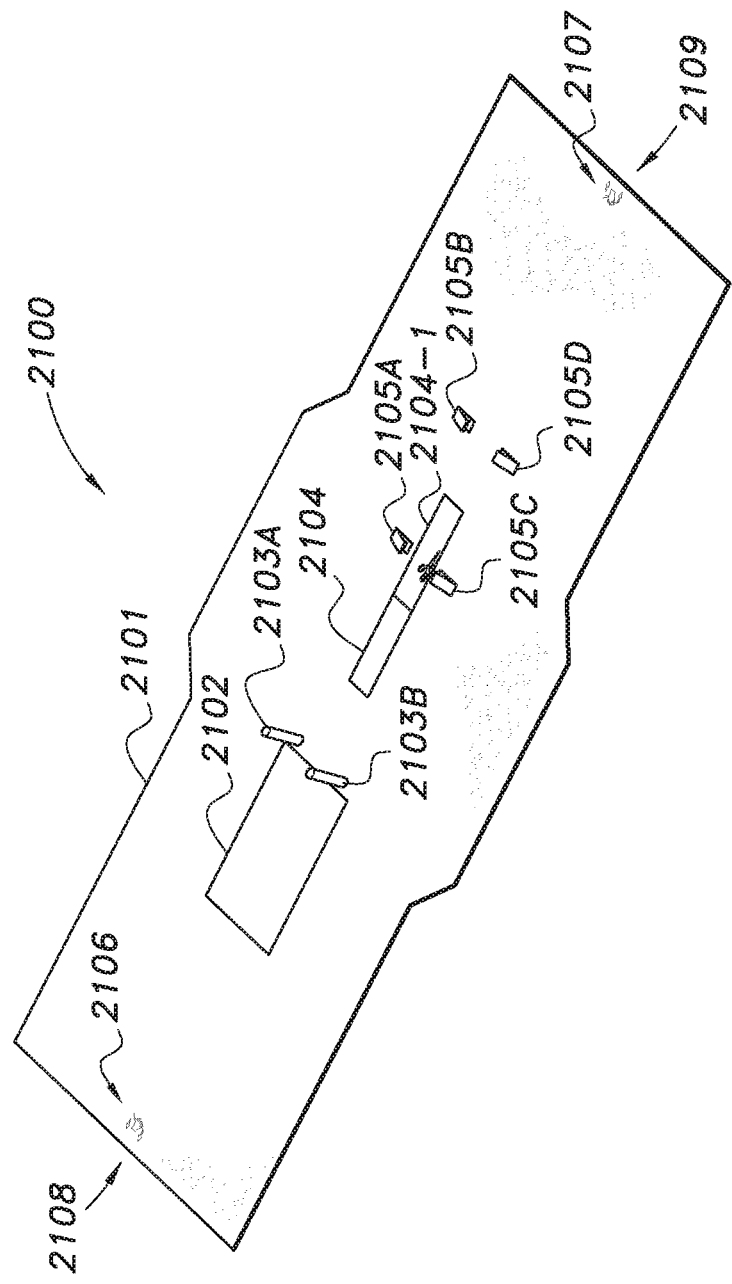
FIG. 21 shows a top side of another embodiment of a surgical drape used with the system or apparatus.

Now referring to FIG. 21, which illustrates a top side of another embodiment of a surgical drape used with the systems or apparatuses disclosed herein. The top side of the surgical drape 2100 includes a drape 2101, a window 2102, one or more covers 2103A, 2103B, a surgical opening 2104, one or more fastener components 2105A-D, and one or more markings 2106, 2107 on a proximal end 2108 and a distal end 2109 of the drape 2101.

The drape embodiment 2101, as illustrated in FIG. 21 is generally rectangular in shape with a certain length and width. The proximal end 2108 and the distal end 2109 of the drape 2101 may be of the same width; however, a center portion of the drape 2101 may include a width that is greater than width of the proximal end 2108 and the distal end 2109 of the drape 2101.

A window 2102 may be included in, and visible on, the top side 2100 of the drape 2101. The window 2102 is transparent and as such acts as a viewing window for a physician to see through and observe activity on the opposite side of the drape 2101. The window 2102 may not be a hole or opening for passing through objects from the top side 2100 to the bottom side 2200 of the drape 2101, but rather may be made of a substantially transparent material. The window 2102 may be rectangular in shape and is positioned closer to the proximal end 2108 of the drape 2101. The window 2102 together with the rest of the drape 2100 acts like a sterile barrier between the top side 2100 and an opposite bottom side 2200 of the drape 2101. One skilled in the art would appreciate that one window 2102 is illustrated in FIG. 21; however, multiple windows with different sizes and configurations may be incorporated in the drape 2100.

Figure 22:
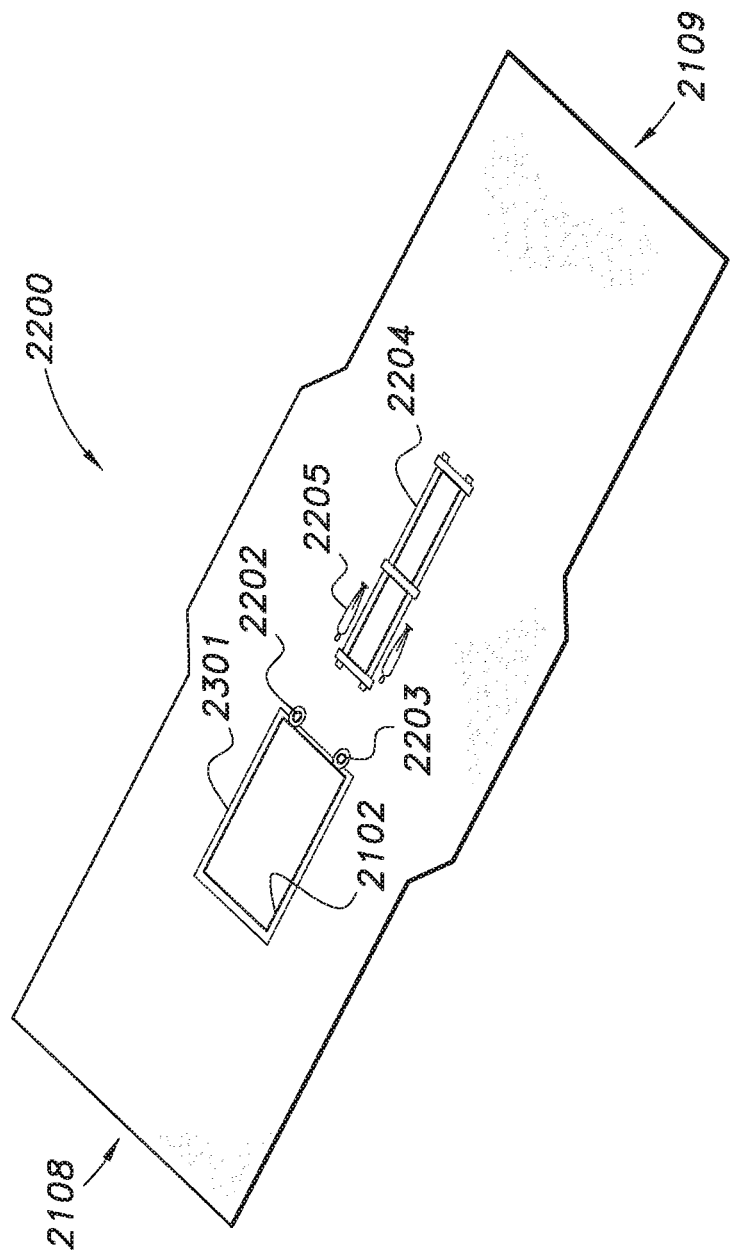
FIG. 22 shows a bottom side of an embodiment the surgical drape shown in FIG. 21 as used with the system or apparatus.

In certain embodiments, one or more covers 2103A, 2103B may be included on the top side of the drape 2101. As shown in FIG. 21, the top side of the drape 2101 includes a right side cover 2103A and a left side cover 2103B. These covers are distal to the window 2102 and extend upwardly in a substantially perpendicular fashion from the top side of the drape 2101. The right side cover 2103A and the left side cover 2103B may be transparent, and may be made of a polyethylene material, or any other flexible material. The right side cover 2103A includes a cover opening 2203 and the left side cover 2103B includes another different cover opening 2202, as illustrated in FIG. 22 and further discussed below. The cover opening 2202 allows passage of one handle, for example handle 242*b* as shown in FIG. 11, such that the handle 242*b* is surrounded by cover 2103A once placed therein, and ready to be engaged by the physician from the top side of the drape 2101. Whereas, the opening 2203 allows passage of a different second handle, for example handle 242*a* as shown in FIG. 11, such that the handle 242*a* is surrounded by the cover 2103B once placed therein, and ready to be engaged by the physician from the top side of the drape 2101.

A surgical opening 2104 may be included through the drape 2101. The surgical opening 2104 is discussed in conjunction with reference to FIG. 23B represented as 2300B. The surgical opening 2104 is positioned distal to the one or more covers 2103A, 2103B such that the one or more covers 2103A, 2103B are positioned in between the window 2102 and the surgical opening 2104 as shown in FIG. 21. The surgical opening 2104 may be substantially rectangular in shape, and may include two segments or sections. The first segment or section consists of a surgical opening or passage through which devices may pass through from the top side 2100 of the drape 2101 to the bottom side 2200 of the drape 2101. The surgical opening allows access to a surgical site such as an incision made on a patient. The incision may be made for example on a neck or upper back region of the patient; however, example embodiments disclosed herein are not limited to these regions. The surgical opening 2104 may also be extendable and include a second surgical opening segment or section 2104-1, which may be represented as dotted lines as shown in FIG. 23B, such that removal of the second surgical opening segment or section 2104-1 can extend the surgical opening between the first section and second surgical opening segment or section 2104-1. For example, if the physician desires an enlarged surgical opening in the surgical opening 2104 region for purposes of increasing flexibility in the work space, enlarging the surgical site, or introducing additional objects there through from the top side 2100 of the drape 2101 to the bottom side 2200 of the drape 2101, the physician may simply remove the second surgical opening segment or section 2104-1 of the drape 2101. Thereby, enlarging the surgical opening 2104. The removal of the second surgical opening segment or section 2104-1 may be accomplished using scissors as shown in FIGS. 21 and 23B, or alternatively other similar means that would be appreciated by one skilled in the art.

In one embodiment, the distance between the surgical opening 2104 and the window 2102 may be spaced apart by approximately fourteen (14) inches or more. One skilled in the art would appreciate to optimize the distance between the surgical opening 2104 and the window 2102 such that during a surgical procedure a patient's head may be able to move rotationally within range of +/−30 degrees without displacing the fabric of the drape 2101 or causing it to tear especially around the regions of the window 2102 and the one or more covers 2103A, 2103B.

Still referring to FIG. 21, in certain embodiments, fastener components 2105A-D may be positioned on the top side of the surgical drape 2101. The fastener components 2105A-D are positioned on the distal end 2109 of the drape 2101 and proximate to the surgical opening 2104. The fastener components 2105A-D hold the objects in place, including objects that may pass through the surgical opening 2104. The objects may include surgical instruments or surgical tools that are required for a surgical procedure. These surgical instruments or surgical tools may include, for example, including but not limited to, suction devices and/or mechanical devices like electric knives or ultrasound probes. The fastener components 2105A-D may secure portions of those objects, for example, tubes or wires. In some embodiments, the fastener components 2105A-D may be, for example, selected from the group comprising hook and loop straps, e.g. Velcro® straps, clips or clamps. Although four fastener components 2105A-D are shown in FIG. 21, one skilled in the art would appreciate that additional fasteners, and addition types of fasteners, may be incorporated as desired. For example, additional fasteners may be incorporated along the window 2102 or one or more covers 2103A, 2103B; and their orientation on the top surface 2100 may be adjusted as desired.

In certain embodiments, one or more markings 2106, 2107 may be included on the top side 2100 of the drape 2101. However, these one or more markings 2106, 2107 may be included on the bottom side 2200 of the drape 2101 as well. For example, marking 2106 may be included on the proximal end 2108 of the drape 2101 and another marking 2107 may be included on the distal end 2109 of the drape 2101. These markings are shown in greater detail FIG. 34. As such, referring to FIG. 21 in conjunction with FIG. 34, the markings 2106, 2107 may represent a hand symbol that is holding the drape 2101 and the direction of arrows which instruct a physician or user to pull the drape 2101 in a certain direction during deployment of the drape. For example, marking 2106 illustrates direction of arrows in one direction and marking 2107 illustrates direction of arrows in an opposite direction to the arrows shown in marking 2106. These markings 2106, 2107 may instruct the physician how to unfold the drape 2101 once taken out of its packaging.

Next, referring to FIG. 22, a bottom side of the drape 2200 is illustrated. In various embodiments, the bottom side of the drape 2200 may include window 2102, additional window material 2301, cover openings 2202, 2203 and adhesive component such as tape 2204 along with markings 2205.

Figure 23:
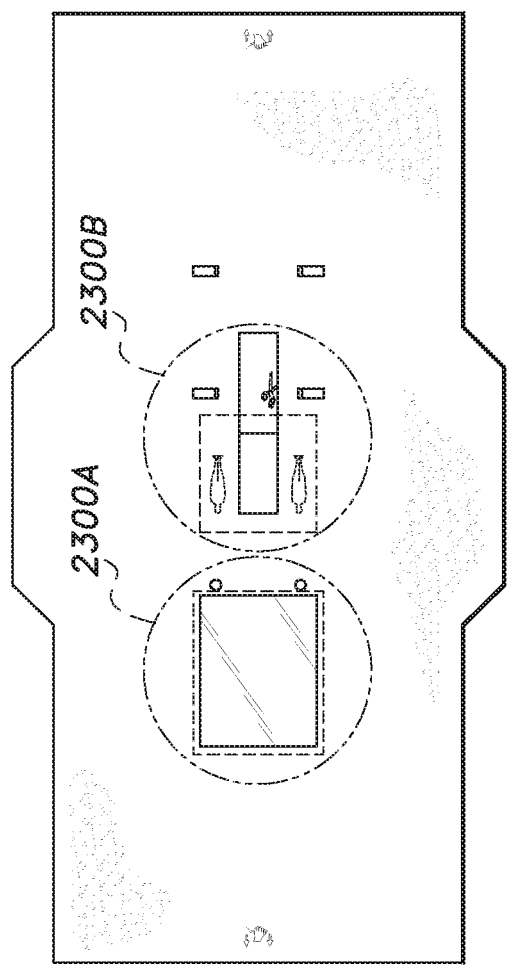
FIG. 23 shows another perspective view of an embodiment of the top side of the surgical drape, illustrating a transparent window and an extendable opening positioned on the top side of the surgical drape.

The aforementioned features may be illustrated and discussed in conjunction with FIGS. 23, 23A, 23B and 23C. FIG. 23 depicts the top side of the surgical drape, illustrating a transparent window and an extendable opening positioned on the top side of the surgical drape 2101 is shown. This representation of the top side 2100 of the drape 2101 illustrates the window 2102 along with additional window material 2301, and the surgical opening 2104 along with markings 2205 on bottom side 2200 of the drape 2101.

In certain embodiments, the window 2102 will be described in conjunction with FIG. 23A, which is shown from the perspective of the top side 2100 of the drape 2101. The window 2102 is placed on the bottom side of the drape 2200. In certain embodiments, the window 2102 is slightly greater in width and length than that of the opening in the drape as shown in FIG. 23A, such that the outline of the additional window material 2301 is indicated. Also, the cover flanges 2302 are greater in diameter than the diameter of the holes 2202, 2203. The window 2102 and the cover flanges 2302 may be bonded to the bottom side of the drape 2200 using a method selected from pressure sensitive adhesives, heat seal adhesives, ultrasonic sealant, and combinations of any thereof. Thereby, securing the window 2102 and the cover flanges 2302 on the bottom side 2200 of the drape 2101. Such securing mechanism is especially important to prevent a tear or rip in the drape 2101, especially around regions of the window 2102 and one or more covers 2103A, 2103B when the drape 2101 is being used for a procedure. One skilled in the art would appreciate that the additional window material 2301 and the covers 2103A, 2103B may be attached to the drape 2101 using other methods known in the art.

The openings 2202, 2203, as discussed above under FIG. 21, allow passage of one or more handles there through such that they can be engaged by a physician from the top side of the device. For example, handles 242*a*, 242*b*, as shown in FIG. 11, may pass through from the bottom side of the drape into the openings 2203, 2203 such that the handles 242*a*, 242*b* are securely positioned in the one or more covers 2103A, 2103B for physician's use.

In certain embodiments, the adhesive component such as tape 2204 and markings 2205 will be described in greater detail in conjunction with FIG. 23C. The tape 2204 and markings 2205 are positioned on the bottom side of the drape 2101 surrounding the surgical opening 2104 and the second surgical opening section 2104-1, and distal to the window 2102. As shown in greater detail in FIG. 23C, the tape 2204 may include longitudinal strips 2304, 2305, 2308, 2309 and horizontal strips 2303, 2306 and 2307. These longitudinal and horizontal strips are positioned on the bottom side 2200 of the drape 2101 surrounding the surgical opening 2104 and second surgical opening section 2104-1 as shown in FIG. 23B. The longitudinal strips 2304, 2305, 2308, 2309 and horizontal strips 2303, 2306 and 2307 may be made adhesive by removing an outer protective covering layer, or liner. The longitudinal strips 2305 and 2308 may constitute two different strips such that they are not connected at the intersection where they meet the horizontal strip 2306. Similarly, horizontal strips 2304 and 2309 may constitute two different strips such that they are not connected at the intersection where they meet the horizontal strip 2306.

Further, the longitudinal strips 2304, 2305 and the horizontal strips 2303, 2306 may be selectively made adhesive, while the longitudinal strips 2308, 2309 and horizontal strips 2306, 2307 may not be made adhesive by having the outer covering removed. For example, if the physician wants to work with a smaller surgical opening 2104, the physician may not remove the outer coverings of longitudinal strips 2308 and 2309 and horizontal strip 2307. Instead, the physician may limit the removal of outer covering of only the longitudinal strips 2304, 2305 and the horizontal strips 2303 and 2306. However, if the physician wants to increase the surgical opening 2104 to include the second surgical opening section 2104-1 to increase the workspace, he/she may remove the second surgical opening section 2104-1 as discussed above with respect to FIGS. 21 and 23B, and additionally remove the outer covering over the longitudinal strips 2308 and 2309 and horizontal strip 2307. Thereby, making the longitudinal strips 2308, 2309, and horizontal strip 2307 adhesive and allowing the physician to secure them on the patient. In this embodiment, horizontal strip 2306 may be removed during the cutting or removal of the second surgical opening section 2104-1. As such the longitudinal and horizontal strips may be selectively releasable as desired by the physician.

Additionally, in certain embodiments, the longitudinal and horizontal strips may include respective pull tabs. To create the pull tab, the adhesive underneath the horizontal or longitudinal strip may not extend to the edge of the strip, thereby allowing an easier grip on the pull tab. For example, strips 2304, 2305, 2308, 2309 may include respective pull tabs 2305-1, 2305-2, 2305-3 and 2305-4, as shown in FIG. 23C. Additional pull tabs (not shown) may also be included on the ends of the horizontal strips 2303, 2306, 2307. These respective pull tabs are used for engaging or holding on to the longitudinal and horizontal strips. In certain embodiments, the respective pull tabs 2305-1, 2305-2, 2305-3 and 2305-4 may or may not be adhesive as they assist the user to engage the respective pull tabs in order to remove an outer covering from the respective longitudinal and horizontal strips in order to uncover or expose the underlying adhesive surface.

Figure 34:
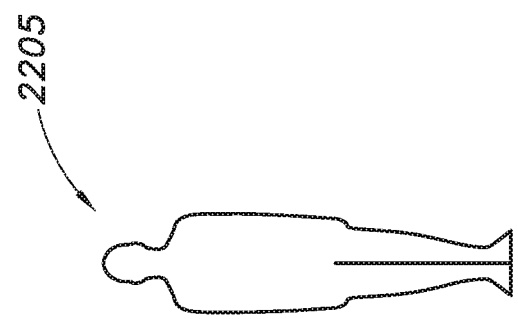
FIG. 34 illustrates an example embodiment of a marking on the bottom side of the surgical drape as illustrated in FIG. 22.
Figure 33:
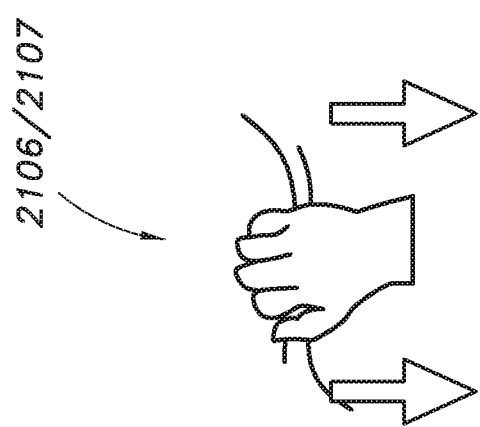
FIG. 33 illustrates an example embodiment of a marking on a proximal end and a distal end of the top side of the surgical drape as illustrated in FIG. 21.

Lastly, with respect to markings 2205, as shown in FIG. 22, 23C and also in FIG. 34, in certain embodiments they may represent the orientation of the patient that should be observed with respect to placing the drape 2201 on the patient. For example, as shown in markings 2205, which depicts a patient, for example, has its head facing in the proximal end 2108 and feet facing in the distal end 2109. Such marking 2205 allows the physician to orient the drape 2201 accordingly during the surgical procedure with respect to the patient such that he/she is able to view the procedure through the window 2102 and engage the handles 242*a*, 242*b* as they pass through one or more covers 2103A, 2103B, and access the surgical site on the patient through surgical opening 2104. One skilled in the art would appreciate that the markings 2205 disclosed herein are not limited to such representation, and similar representations may be undertaken.

Figure 24:
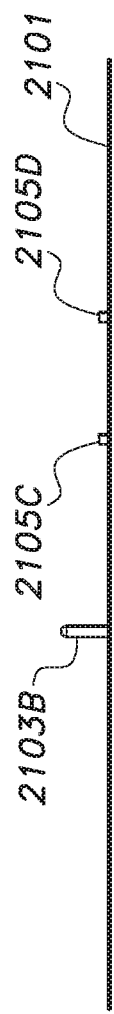
FIG. 24 illustrates a side view of an embodiment of the surgical drape.

Next, with respect to FIG. 24 a side view of an embodiment the drape 2101 is shown, wherein one cover 2103B is visible along with two of the adhesive components 2105C, 2105D.

Figure 24A:
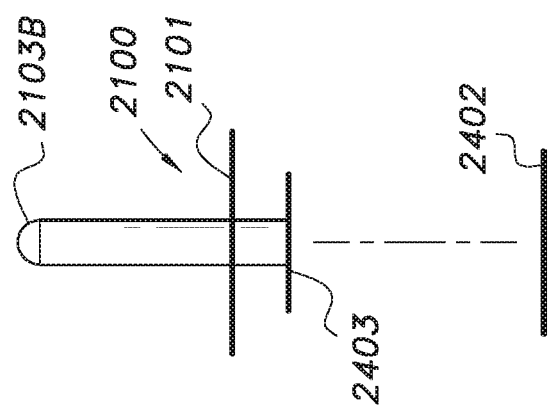
FIG. 24A illustrates a side exploded view of an embodiment of the cover and its relationship to the surgical drape as shown in FIG. 21.

Illustrating one embodiment of the cover 2103B in greater detail is an exploded view shown in FIG. 24A. The cover 2103B includes a first segment that extends above the top surface 2100 of the drape 2101 as shown in FIG. 24A. A second segment includes a flange 2403 of the cover 2103B. The flange 2403 of the cover 2103B is below the top surface of the drape 2101. Further, this embodiment may include one or more adhesive components 2402. These adhesive components 2402 being a single sided tape spaced apart from the flange 2403. The cover 2103B illustrated in FIG. 24A is not drawn to scale, and the length of drape 2101 may be longer than the flange 2403, and length of the one or more adhesive components 2402 may be longer than the length of the flange 2403 but shorter than the length of the drape 2101. The structural components described herein with respect to cover 2103B also similarly apply to the other cover 2103A. In this embodiment, the flange 2403 may be bonded to the bottom surface 2200 of the drape 2101 by pressure sensitive adhesives, heat sensitive adhesives, ultrasonic sealant, and any combinations thereof. The flange 2403 may be bonded between the bottom side 2200 of the drape 2101 and optionally a tape 2402 on the opposite side of the flange 2403. The tape 2402 may overlap the flange 2403 onto the bottom side 2200 of the drape 2101.

Next with respect to FIGS. 25 and 26, a folding embodiment of drape 2101 is shown. FIG. 25 illustrates the drape 2101 positioned flat on a surface extending from the proximal end 2108 to the distal end 2109 with the bottom surface 2200 of the drape 2101 facing the physician. The dotted lines represented in FIG. 25 represented the accordion style fold that is undertaken to wrap or fold the drape 2101. FIG. 26 is a side view of the drape 2101 as shown in FIG. 25 as it is folded inward from either ends towards the center, or as it is being unfolded.

Now, disclosure with respect to folding and packaging of certain embodiments of the drape 2101 will be discussed with reference to FIGS. 24-32. FIG. 27 represents a side view 2700 of the drape 2101 as it is folded inward. With respect to folding the drape 2101 the physician, user or technician may start from the proximal end 2108 and the distal end 2109 of the drape 2101 as the bottom side 2200 of the drape 2101 is facing the user as shown in FIG. 25. The user may fold inward proximal most end on the proximal end and distal most end on the distal end of the drape 2101 by having such ends face inward. The user may fold the proximal most end and the distal most end simultaneously or independently of each other. When folding the proximal most end and the distal most end, the user may undertake an accordion style fold, as shown in FIG. 26, such that such ends are parallel along a surface of the drape 2101. The proximal most end is folded inward in accordion style until the proximal end 2108 reaches a center of the drape as shown in FIG. 27. And, the distal most end is folded inward in accordion style until the distal end 2109 reaches the center of the drape as shown in FIG. 27.

By having the proximal end 2108 and distal end 2109 folded in an accordion style until they reach the center of the drape 2101, a stack of the drape 2101 is obtained with a head-end stack and a foot-end stack as shown in FIG. 28. The illustration shown in FIG. 28 is a partially folded configuration 2800, wherein a gap is maintained along the orthogonal axis of bottom surface of the drape 2101 between the head-end stack and the foot-end stack. FIG. 29 illustrates another cross-sectional view 2900 of the partially folded configuration 2800 as shown in FIG. 28. In particular, FIG. 29 illustrates an orthogonal view showing the partially folded configuration 2800 having additional folds with the seam oriented medially. Each lateral side stack is folded several times medially until the configuration 2900, shown in FIG. 29, is achieved.

After achieving such partial fold configuration 2900, each lateral drape stack is folded one more time along the medial axis of the bottom surface of the drape 2101. As shown in in FIG. 30, one embodiment of the complete and final fold configuration 3000 is shown, wherein each lateral side stack is folded along the medial axis of the bottom surface of the drape 2101. Thereby, resulting in a compact configuration of the drape 2101 for purposes of easy packaging, shipping and handling.

With respect to FIG. 31, a top view of the surgical drape 2101 as folded in orthogonal fashion as shown in FIG. 30 is illustrated. After the surgical drape 2101 achieves the final fold configuration 3000, it is placed in a package 3101 such that from the top view 3100 of the package 3101, a user can see the marking 2205, which aids the user in orienting the drape 2101.

Figure 32:
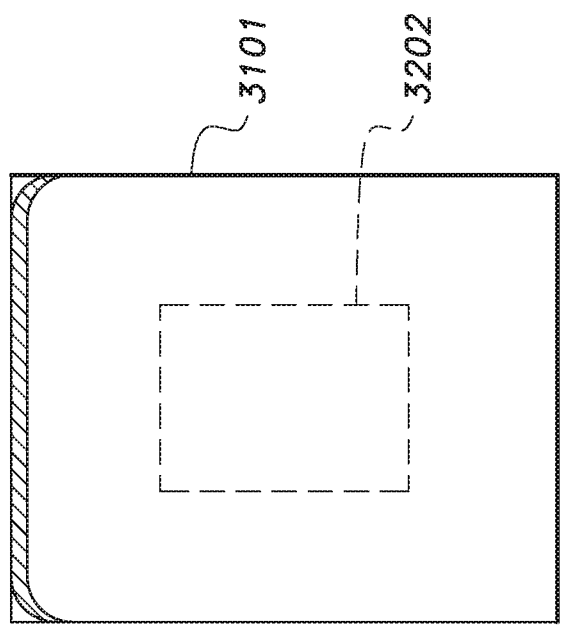
FIG. 32 illustrates a perspective view of an embodiment of packaging for placing the surgical drape therein.

With respect to FIG. 32, a side view of the package 3101 is shown with a product label or instructions for use 3202 on the side of the package 3101. As such, a manufacturer or maker of the drape may package the drape 2101 in a package 3101 that fits the drape 2101 in its final fold configuration 3000.

Now, the use of an embodiment of the drape 2101 for a surgical procedure, for example, will be described. A physician, a user or a technician may take out the drape 2101 from the package 3101 after reading the instructions 3202 on the package 3101. The drape 2101 may include a further protective wrapping which would need to be removed before using the drape 2101. The drape 2101, after removal from the package 3101, will be in the final folded configuration 3000 as shown in FIG. 30; and the physician will be able to view the marking 2205 from a top view as shown in FIG. 31, which will aid the physician to orient the drape 2101 with respect to the patient. Being in book-like fashion would allow the user to easily handle and maneuver the drape 2101 out of the package 3101. Next, the user or physician will align the surgical opening 2104 shown in FIGS. 21 and 23B over a surgical site and position the drape 2101 around the surgical site. Thereafter, the user may remove outer protective covering from the longitudinal strips 2304, 2305 and the horizontal strips 2303, 2306 such that the underlying adhesive layer is exposed and ready for use. The user may also remove a release paper covering a top side or a bottom side of window 2102.

After orienting the drape 2101 relative to the markings 2205, the user may place the longitudinal strips 2304, 2305 and the horizontal strips 2303, 2306 around an incision site or the site of interest such that the surgical opening 2104 on the top side 2100 of the drape 2101 is around the incision site. Thereby, allowing the physician or user to view and access the incision site.

Next, the user will unfold the drape 2101 along orthogonal and parallel axis of the drape 2101. In other words, resulting in having the drape 2101 unfold that would result in configuration of the drape 2101 shown in FIGS. 27, 28 and 29. After the drape 2101 is in this partially unfolded configuration, the user will identify markings 2106, 2107 on top surface 2100 of the drape 2101. Identifying such markings 2106, 2107, would indicate to the user to pull the proximal end 2108 and the distal end 2109 to patient's foot-end and head-end of the table on which the patient is placed. Thereby, allowing the drape 2101 to be entirely unfolded and is flat on a surface as shown in FIG. 25.

If the user or physician determines that the surgical opening 2104 needs to be widened or made bigger in order to increase the working space or allow additional objects to pass there through, the user or physician may remove the second surgical opening section 2401-1 as shown in FIG. 23B. By removing the second surgical opening section 2401-1 the surgical opening 2104 can be made bigger such that working space for the physician is increased. Thereby, the user may enlarge the incision site or introduce additional objects through the opening.

After the bottom side 2200 of the drape 2101 is in place and the surgical opening 2104 in the correct position, the user may introduce handles 241a, 241b from the bottom side 2200 of the drape 2101 and have the handles 241a, 241b pass through the openings 2202, 2203 such that the handles 241a, 241b are placed in the respective covers 2103A, 2103B. Once the handles 241*a*, 241*b* are in position in the respective covers 2103A, 2103B, the physician may engage with the handles 241*a*, 241*b* and accordingly maneuver a patient's head or alternatively perform the desired surgical procedures as he/she views through the window 2102. Lastly, the user may engage objects such as surgical instruments or tools with the fastener components 2105A-D such that such objects are securely positioned in place for use during a procedure.

It will be appreciated by those skilled in the art that changes could be made to the embodiments described above without departing from the broad inventive concept thereof. For example, various mechanical and electrical connection elements and actuators can be used to achieve the disclosed function. It is understood, therefore, that this invention is not limited to the particular embodiments disclosed, but it is intended to cover modifications within the spirit and scope of the present invention as defined by the appended claims.

What is claimed is:

1. A drape for use in a surgical procedure, comprising:
   a top surface and an opposite bottom surface, the bottom surface configured to contact a patient during the surgical procedure, the top surface configured to engage with a physician during the surgical procedure, the top surface and the bottom surface extending between a proximal end and a distal end of the drape;
   one or more surgical openings positioned by the distal end of the drape; and
   one or more covers on the top surface of the drape, the one or more covers extending perpendicularly upward from the top surface of the drape.

2. The drape of claim 1, wherein,
   the one or more covers includes a first cover and a different second cover,
   the first cover configured to receive from the bottom surface of the drape a first control handle through a first opening, the first opening formed between the top surface and the bottom surface of the drape, and
   the second cover configured to receive from the bottom surface of the drape a different second control handle through a second opening, the second opening formed between the top surface and the bottom surface of the drape.

3. The drape of claim 1, further comprising:
   one or more fastener components on the top surface and positioned by the distal end of the drape, the one or more fastener components configured to engage one or more objects such that position of the one or more objects are maintained.

4. The drape of claim 1, further comprising:
   an adhesive component on the bottom surface and positioned by the distal end of the drape; and
   one or more markings configured to identify position of the patient relative to the drape, the one or more markings positioned by the distal end of the drape and adjacent to the adhesive component.

5. The drape of claim 1, further comprising:
   one or more adhesive components on the bottom surface and positioned by the distal end of the drape, the one or more adhesive components including a first adhesive component and a different second adhesive component, the second adhesive component selectively releasable independent of the first adhesive component.

6. The drape of claim 1, wherein the one or more surgical openings are configured to be extended from a first length to a second length, the second length being greater than the first length.

7. The drape of claim 1, wherein the one or more covers includes a first portion extending above the top surface, and a second portion corresponding to a flange, the flange being bonded to the drape.

8. The drape of claim 1, wherein the one or more surgical openings are configured to receive one or more objects such that the one or more objects passes from the top surface to the bottom surface.

9. The drape of claim 8, wherein the one or more objects corresponds to a respective surgical tool, the respective surgical tool being selected from the group consisting of suction devices, mechanical devices, electric knives and ultrasound probes.

10. The drape of claim 1, wherein the one or more covers includes a first cover spaced apart from a different second cover such that the first cover is configured to receive a first handle from the bottom surface and the second cover is configured to receive a different second handle from the bottom surface.

11. The drape of claim 1, further comprising:
    one or more windows, the one or more windows being transparent, the one or more windows being positioned by the proximal end of the drape, wherein the one or more surgical openings are spaced apart from the one or more windows.

12. The drape of claim 11, wherein the one or more covers are positioned between the one or more windows and the one or more surgical openings.

13. The drape of claim 1, wherein the one or more surgical openings are positioned distal to the one or more covers.

14. A drape for use in a surgical procedure, comprising:
    a top surface and an opposite bottom surface, the bottom surface configured to contact a patient during the surgical procedure, the top surface configured to engage with a physician during the surgical procedure, the top surface and the bottom surface extending between a proximal end and a distal end of the drape;
    one or more surgical openings; and
    one or more covers on the top surface of the drape, the one or more covers extending perpendicularly upward from the top surface of the drape.

15. The drape of claim 14, wherein,
    the top surface of the drape is configured to be folded in an accordion fashion such that the proximal end and the distal end are folded inward toward a center of the drape,
    the proximal end of the top surface is configured to fold inward toward the center of the drape such that a proximal most end of the proximal end is folded inward parallel to the top surface, and the distal end of the top surface is configured to fold inward toward the center of the drape such that a distal most end of the distal end is folded inward parallel to the top surface, and
    the drape comprises one or more adhesive components on the bottom surface of the drape, wherein,
        the proximal end is configured to be folded perpendicular to the top surface after the proximal most end is folded inward toward the center of the drape such that the proximal most end faces the one or more adhesive components, and
        the distal end is configured to be folded perpendicular to the top surface after the distal most end is folded inward toward the center of the drape such that the distal most end faces the one or more adhesive components.

16. The drape of claim 14, further comprising:
one or more windows on the top surface of the drape, the one or more windows being transparent, the one or more windows being positioned by the proximal end of the drape.

17. The drape of claim 14, wherein the one or more surgical openings are positioned distal to the one or more covers.

18. A method of folding a drape, comprising:
folding a proximal most end of the drape from a proximal end of the drape to a center of the drape in an accordion fashion, the folding of the proximal most end being parallel to a top surface of the drape, the folding of the proximal most end of the drape forming a first lateral side stack, the drape comprising a bottom surface opposite to the top surface, the bottom surface configured to contact a patient during a surgical procedure, the top surface configured to engage with a physician during the surgical procedure, the top surface and the bottom surface extending between the proximal end and a distal end of the drape;

folding a distal most end of the drape from the distal end of the drape to the center of the drape in the accordion fashion, the folding of the distal most end being parallel to the top surface of the drape, the folding of the distal most end of the drape forming a different second lateral side stack;

folding the first lateral side stack along a medial axis of the top surface of the drape; and folding the second lateral stack along the medial axis of the top surface of the drape towards the first lateral side stack, wherein the drape comprises, one or more surgical openings; and one or more covers on the top surface of the drape, the one or more covers extending perpendicularly upward from the top surface of the drape.

19. The method of claim 18, further comprising:
identifying a first marking on the proximal most end of the drape prior to the folding of the proximal most end; and identifying a different second marking on the distal most end of the drape prior to the folding of the distal most end.

20. The method of claim 18, wherein the drape comprises, one or more windows on the top surface of the drape, the one or more windows being transparent, the one or more windows being positioned by the proximal end of the drape.

21. The method of claim 18, wherein the one or more surgical openings are positioned distal to the one or more covers.

* * * * *